(12) United States Patent
Newmark et al.

(10) Patent No.: US 8,114,446 B2
(45) Date of Patent: *Feb. 14, 2012

(54) METHODS FOR MODULATING EICOSANOID METABOLISM

(75) Inventors: Thomas Newmark, Brattleboro, VT (US); Paul Schulick, Brattleboro, VT (US); Robert Newman, Houston, TX (US); Bharat Aggarwal, Houston, TX (US)

(73) Assignees: New Chapter Inc., Brattleboro, VT (US); Board Of Regents Of The University Of Texas System, Austin, TX (US)

( * ) Notice: Subject to any disclaimer, the term of this patent is extended or adjusted under 35 U.S.C. 154(b) by 0 days.
This patent is subject to a terminal disclaimer.

(21) Appl. No.: 12/826,289

(22) Filed: Jun. 29, 2010

(65) Prior Publication Data
US 2011/0020479 A1    Jan. 27, 2011

Related U.S. Application Data

(63) Continuation of application No. 12/318,389, filed on Dec. 29, 2008, which is a continuation of application No. 11/452,246, filed on Jun. 14, 2006, now Pat. No. 7,563,462.

(60) Provisional application No. 60/690,161, filed on Jun. 14, 2005, provisional application No. 60/792,330, filed on Apr. 17, 2006.

(51) Int. Cl.
*A61K 36/82* (2006.01)
*A61K 36/53* (2006.01)
*A61K 36/906* (2006.01)
*A61K 36/00* (2006.01)

(52) U.S. Cl. ........ 424/729; 424/745; 424/756; 424/777; 424/725

(58) Field of Classification Search .................. None
See application file for complete search history.

(56) References Cited

U.S. PATENT DOCUMENTS

| | | | |
|---|---|---|---|
| 6,261,607 B1 | 7/2001 | Newmark et al. | |
| 6,387,416 B1 | 5/2002 | Newmark et al. | |
| 6,488,957 B1 | 12/2002 | Koumarianos | |
| 6,541,045 B1 | 4/2003 | Charters et al. | |
| 6,596,313 B2 * | 7/2003 | Rosenbloom | 424/464 |
| 7,067,159 B2 | 6/2006 | Newmark et al. | |
| 7,070,816 B2 | 7/2006 | Newmark et al. | |
| 7,470,440 B2 | 12/2008 | Newmark et al. | |
| 7,563,462 B2 | 7/2009 | Newmark et al. | |
| 7,622,142 B2 * | 11/2009 | Newmark et al. | 424/756 |
| 7,744,931 B2 * | 6/2010 | Newmark et al. | 424/725 |
| 7,744,934 B2 * | 6/2010 | Newmark et al. | 424/725 |

OTHER PUBLICATIONS

Third Party submission in USPTO from V.K. Gupta for U.S. Appl. No. 12/318,389. Letter from V.K. Gupta dated Dec. 28, 2010 with the following cited exhibits. Letter from V.K. Gupta to the USPTO dated Jan. 13, 2011, with USPTO remarks indicating protest denied as untimely. 7 pages.
Bhārata Bhaisajya Ratnākara—Compiled by Nagīnadāsa Chaganalāla Sāha, Translated by Gopinath Gupta—vol. IV: B. Jain Publishers, New Delhi, Edn. 2nd. Reprint, Aug. 1999. [This book contains back references from 1000 B.C. to 20th century] p. 298-299. Formulation Id: RS/808. Formulation Name: Yogottamāgutikā. Publication: p. No. 4 of 29. English Translation including Terminology Conversion (TKDL Extracts): p. No. 5 to 7 of 29.
Bhārata Bhaisajya Ratnākara—Compiled by Nagīnadāsa Chaganalāla Sāha, Translated by Gopinath Gupta—vol. -V: B. Jain Publishers, New Delhi, Edn. 2nd. Reprint, Aug. 1999. [This book contains back references from 1000 B.C. to 20th century] p. 762. Formulation Id: SJ/597. Formulation Name: Kāmakalāvatī. Publication: p. No. 8 of 29. English Translation including Terminology Conversion (TKDL Extracts): p. No. 9 to 11 of 29.
Rasayoga Sāgara—Compiled and Translated by Vaidya Pandita Hariprapanna Jī, vol. II: Krishnadas Academy, Varanasi, Edn. Reprint, 1998. [This book contains back references from 1000 B.C.to 20th century] p. 282. Formulation Id: VS/934. Formulation Name: Lavangapākah). Publication: p. No. 12 of 29. English Translation including Terminology Conversion (TKDL Extracts): p. No. 13 to 15 of 29.
Bhārata Bhaisajya Ratnākara—Compiled by Nagīnadāsa Chaganalāla Sāha, Translated by Gopinath Gupta—vol. I: B. Jain Publishers, New Delhi, Edn. 2nd. Reprint, Aug. 1999. [This book contains back references from 1000 B.C. to 20th century] p. 57. Formulation Id: AB/157. Formulation Name: Agnighrtam (02). Publication: p. No. 16 of 29. English Translation including Terminology Conversion (TKDL Extracts): p. No. 17 to 19 of 29.
Govinda Dāsa; Bhaisajya Ratnāvalī—Edited by Rajeshvaradutta Shastri, Translated by Ambikaduttashastri: Chaukhamba Sanskrit Sansthan, Varanasi, Edn. 14th, 2001. [This book contains back references from 1000 B.C.to 18th century] p. 583. Formulation Id: AK/2635. Formulation Name: Kāñcanāragugguluh. Publication: p. No. 20 of 29. English Translation including Terminology Conversion (TKDL Extracts): p. No. 21 to 22 of 29.
Trimalla Bhatta; Yogatrangini—Commentary by Duttarama Mathura; Chaukhamba Vidyabhavan, Varanasi, Edn. Reprint 2003 p. 131. Formulation Id: AK10/234. Formulation Name: Surana Pidika. Publication: p. No. 23 of 29. English Translation including Terminology Conversion (TKDL Extracts): p. No. 24 to 25 of 29. Sodhala; Gadanigrahah ed, Ganga Sahaya Pandeya & Com.—Indradeva Tripathi, Part-1 (Prayoga Khanda) Chaukhamba Sanskrit Sansthan, Varanasi, Ed. 3rd 1999 p. 97-98. Formulation Id: AK2/141. Formulation Name: Ashvagandhadyam Tailam. Publication: p. No. 26 of 29. English Translation including Terminology Conversion (TKDL Extracts): p. No. 27 to 29 of 29.
Letter from V.K. Gupta dated Nov. 25, 2010 with the following cited ten (10) exhibits to the Canadian Intellectual Property Office; a Third Party Observation under Section 34.1 of the Patent Act of Canada from V.K. Gupta regarding WO 2002/080682; Annex-I (Providing general summary of Traditional Knowledge Digital Library [TKDL] and Indian Systems of Medicine); and Annex-II (Providing English language summary of each exhibit). 13 pages total. Sodhala; Gadanigrahah ed, Ganga Sahaya Pandeya & Com.—Indradeva Tripathi, Part-1 (Prayoga Khanda) Chaukhamba Sanskrit Sansthan, Varanasi, Ed. 3rd 1999 p. 97-98. Formulation Id: AK2/141. Formulation Name: Ashvagandhadyam Tailam. Publication: p. No. 26 of 29. English Translation including Terminology Conversion (TKDL Extracts): p. No. 27 to 29 of 29.

(Continued)

*Primary Examiner* — Christopher R. Tate
(74) *Attorney, Agent, or Firm* — The Nath Law Group; Jerald L. Meyer; Robert M. Joynes

(57) ABSTRACT

The inventive subject matter relates to methods for modulating an eicosanoid metabolic process in cells of an animal in need thereof, which comprises administering to the animal an amount of the inventive compositions effective for regulating the activity of an eicosanoid oxygenase. In particular, the inventive subject matter relates to methods for modulating arachadonic acid metabolism by administering an amount of the inventive compositions effective for regulating the activity of lipoxygenases and cyclooxygenases.

18 Claims, 23 Drawing Sheets

OTHER PUBLICATIONS

Letter from V.K. Gupta dated Nov. 25, 2010 with the following cited ten (10) exhibits to the Canadian Intellectual Property Office; a Third Party Observation under Section 34.1 of the Patent Act of Canada from V.K. Gupta regarding WO 2002/080682; Annex-I (Providing general summary of Traditional Knowledge Digital Library [TKDL] and Indian Systems of Medicine); and Annex-II (Providing English language summary of each exhibit). 13 pages total.

Muheet-e-Azam, vol. I (19th century AD, by Mohammad Azam Khan; Matba Nizami, Kanpur, 1896 A.D. p. 129-130. Formulation ID: MH3/72G. Formulation Name: Zimaad Adrak. p. 5; English translation including Terminology Conversion (TKDL extracts): p. 6; (English summary provided in Annex-II, p. 1, Exhibit 1.).

Bhārata Bhaisajya Ratnākara—Compiled by Nagīnadāsa Chaganalāla Sāha, Translated by Gopinath Gupta—vol. I: B. Jain Publishers, New Delhi, Edn. 2nd. Reprint, Aug. 1999. [This book contains back references from 1000 B.C. to 20th century] p. 302. Formulation ID: AB/100. Formulation Name: Agastimodakah. p. 7; English translation including Terminology Conversion (TKDL extracts): pp. 8-9; (English summary provided in Annex-II, p. 1, Exhibit 2.).

Khazaain-al-Advia, vol. III (20th century AD) by Mohammad Najmul Ghani Khan; Nadeem Yunus Printer / Sheikh Mohd Basheer & Sons, Lahore, 1926 A.D. p. 1050. Formulation ID: JA6/1040E. Formulation Name: Takmeed Bara-e-taskeen. p. 10; English translation including Terminology Conversion (TKDL extracts): p. 11; (English summary provided in Annex-II, p. 1, Exhibit 3.)

Bhārata Bhaisajya Ratnākara—Compiled by Nagīnadāsa Chaganalāla Sāha, Translated by Gopinath Gupta—vol. I: B. Jain Publishers, New Delhi, Edn. 2nd. Reprint, Aug. 1999. [This book contains back references from 1000 B.C. to 20th century] p. 149. Formulation ID: AB/418. Formulation Name: Āgāradhūmatailam. p. 12; English translation including Terminology Conversion (TKDL extracts): pp. 13-14; (English summary provided in Annex-II, p. 2, Exhibit 4.).

Muheet-e-Azam, vol. I (19th century AD) by Mohammad Azam Khan; Matba Nizami, Kanpur, 1896 A.D. p. 188. Formulation ID: MH3/166B. Formulation Name: Zimaad-e- Iklil-ul- Jabal. p. 15; English Translation including Terminology Conversion (TKDL extracts): p. 16; (English summary provided in Annex-II, p. 2, Exhibit 5.)

Khazaain-al-Advia, vol. III (20th century AD) by Mohammad Najmul Ghani Khan; Nadeem Yunus Printer / Sheikh Mohd Basheer & Sons, Lahore, 1926 A.D. p. 780. Formulation ID: JA6/744M. Formulation Name: Zimaad E Marzanjosh. p. 17; English translation including Terminology Conversion (TKDL extracts): p. 18; (English summary provided in Annex-II, p. 2, Exhibit 6.)

Ilaaj-al-Amraaz (18th century A.D.) by Mohammad Shareef Khan; Afzal-al-Matabe, Barqi Press, Delhi, 1921 A.D. p. 307. Formulation ID: MH1/3553. Formulation Name: Zimaad Bara-e- Mafaasil. p. 19; English translation including Terminology Conversion (TKDL extracts): p. 20-21; (English summary provided in Annex-II, p. 3, Exhibit 7.).

Bhārata Bhaisajya Ratnākara—Compiled by Nagīnadāsa Chaganalāla Sāha, Translated by Gopinath Gupta—vol. II: B. Jain Publishers, New Delhi, Edn. 2nd. Reprint, Aug. 1999. [This book contains back references from 1000 B.C. to 20th century) p. 31. Formulation ID: BP/174. Formulation Name: Gomūtramandūram. p. 22; English translation including Terminology Conversion (TKDL extracts): pp. 23-24; (English summary provided in Annex-II, p. 3, Exhibit 8.)

Khazaain-al-Advia, vol. II (20th century A.D.) by Mohammad Najmul Ghani Khan; Nadeem Yunus Printer / Sheikh Mohd Basheer & Sons, Lahore, 1911 A.D. p. 186-187. Formulation ID: AN2/172T. Formulation Name: Zimaad-e-Tulsi Bara-e- Tahleel-e- Waram. p. 25; English translation including Terminology Conversion (TKDL extracts): p. 26; (English summary provided in Annex-II, p. 3, Exhibit 9.)

Khazaain-al-Advia, vol. II (20th century A.D.) by Mohammad Najmul Ghani Khan; Nadeem Yunus Printer I Sheikh Mohd Basheer & Sons, Lahore, 1911 A.D. p. 342-43. Formulation ID: AN2/324. Formulation Name: Chai. p. 27; (English summary provided in Annex-II, p. 4, Exhibit 10.)

* cited by examiner

RANKL (5 nM)   RANKL+Zyflamend

Medium   Zyflamend (0.8 mg/ml)

Fig. 18A
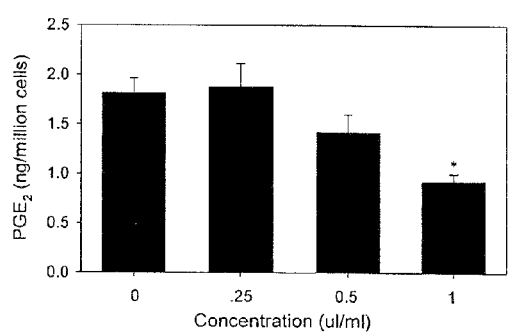
Fig. 18B
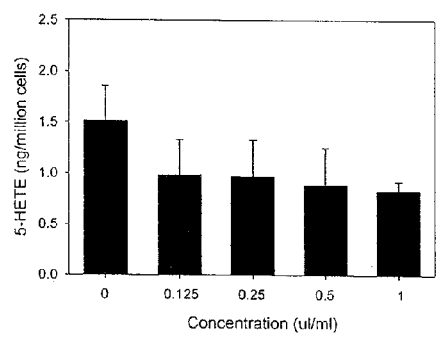
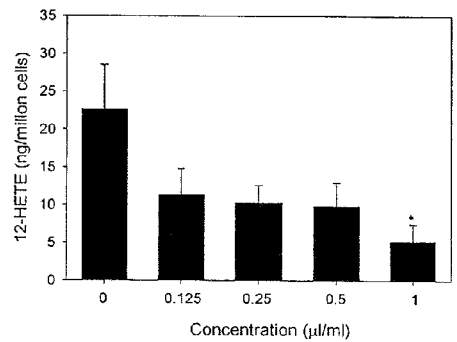
Fig. 18C
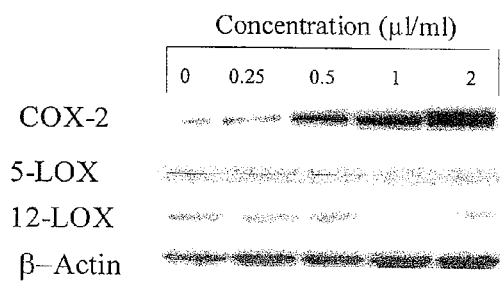
Fig. 18D

SEQUENCE LISTING

```
<160> NUMBER OF SEQ ID NOS: 2

<210> SEQ ID NO 1
<211> LENGTH: 45
<212> TYPE: DNA
<213> ORGANISM: Human immunodeficiency virus
<220> FEATURE:
<221> NAME/KEY: NF-kappaB-binding site
<222> LOCATION: (10)..(19)
<220> FEATURE:
<221> NAME/KEY: NF-kappaB-binding site
<222> LOCATION: (24)..(33)

<400> SEQUENCE: 1
ttgttacaag ggactttccg ctggggactt tccagggagg cgtgg          45

<210> SEQ ID NO 2
<211> LENGTH: 45
<212> TYPE: DNA
<213> ORGANISM: Artificial Sequence
<220> FEATURE:
<223> OTHER INFORMATION: Mutated human immunodeficiency virus long
      terminal repeat
<220> FEATURE:
<221> NAME/KEY: Modified NF-kappaB-binding site
<222> LOCATION: (10)..(19)
<220> FEATURE:
<221> NAME/KEY: Modified NF-kappaB-binding site
<222> LOCATION: (24)..(33)

<400> SEQUENCE: 2
ttgttacaac tcactttccg ctgctcactt tccagggagg cgtgg          45
```

METHODS FOR MODULATING EICOSANOID METABOLISM

This application is a continuation of U.S. patent application Ser. No. 12/318,389, filed Dec. 29, 2008, which is a continuation of U.S. application Ser. No. 11/452,246, filed Jun. 14, 2006 now U.S. Pat No. 7,563,462, which claims benefit of U.S. Provisional Patent Application No. 60/690,161, filed Jun. 14, 2005, and claims benefit of U.S. Provisional Application No. 60/792,330, filed Apr. 17, 2006, the contents of which are hereby incorporated by reference in their entirety.

BACKGROUND OF THE INVENTIVE SUBJECT MATTER

1. Field of Inventive Subject Matter

The inventive subject matter relates to methods for modulating an eicosanoid metabolic process in cells of an animal in need thereof, which comprises administering to the animal an amount of the inventive compositions effective for regulating the activity of an eicosanoid oxygenase. In particular, the inventive subject matter relates to methods for modulating arachidonic acid metabolism by administering an amount of the inventive compositions effective for regulating the activity of lipoxygenases and cyclooxygenases.

2. Background

Although progress has been made in the early diagnosis and treatment of cancers such as prostate cancer, prostate cancer remains the most common malignancy and the second leading cause of male cancer related deaths in the United States. One of the more interesting aspects of this disease is the fact that latent prostate cancer occurs at equal rates in both Asian and American men, while the incidence of clinically significant prostate cancer is much greater in the US than in Asia. There are many reasons to believe that this discrepancy is related to the dietary intake of different populations and these observations have stimulated extensive research into various dietary factors that might influence progression of prostate cancer. Some epidemiological studies suggest this may be in part due to the lower fat intake in Asian diets compared to the typical Western diet, as high fat diets have been linked to elevated risks of prostate cancer.

Applicants have found that administration of the inventive compositions inhibits TNF-induced NF-κB activation in myeloid leukemia KBM-5 cells and cigarette smoke condensate-induced NF-κB activation in lung adenocarcinoma H1299 cells. Administration of the inventive compositions also leads to suppression of TNF-induced cell invasion and abrogated RANKL-induced osteoclastogenesis. Further, administration of the inventive compositions suppresses TNF-induced expression of various antiapoptotic, proliferative, and metastasis gene products.

SUMMARY OF THE INVENTIVE SUBJECT MATTER

The inventive subject matter relates to a method for modulating an eicosanoid metabolic process in cells of an animal in need thereof, which comprises administering to the animal an amount of a composition effective for regulating the activity of an eicosanoid oxygenase,
   wherein the composition comprises therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

The inventive subject matter further relates to a method of delivering 13-S-HODE to an animal in need thereof, comprising administering to the animal a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

Additionally, the inventive subject matter relates to a method for inhibiting arachidonic acid-mediated inflammation in an animal in need thereof, comprising administering to the animal a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

Furthermore, the inventive subject matter relates to a method for modulating the level of NF-κB-regulated gene products in cells of an animal in need thereof, comprising administering to the animal a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

BRIEF DESCRIPTION OF THE DRAWINGS

FIG. 16(A) depicts a normal cell cycle distribution of PC3 cells. In FIG. 16(B), the size of the G2/M peak increases. FIG. 16(C) and FIG. 16(D) show an increasing cell cycle block due to increased concentration of the inventive compositions.

FIG. 17(B)=0.28 ul/ml; FIG. 17(C)=0.57 ul/ml; FIG. 17(D)=1.14 ul/ml) and then stained with Annexin V and PI solution.

FIG. 18(A) is a graph depicting the formation of $PGE_2$ in relation to the concentrations of the inventive compositions shown.

FIG. 18(B) is a graph depicting the formation of 5-HETE in relation to the concentrations of the inventive compositions shown.

FIG. 18(C) is a graph depicting the formation of 12-HETE in relation to the concentrations of the inventive compositions shown.

FIG. 18(D) is a photograph of a Western blot depicting treatment of PC3 cells with the inventive compositions and the cellular content of 5-LOX protein.

DETAILED DESCRIPTION OF THE INVENTIVE SUBJECT MATTER

Definitions

Figure 1:
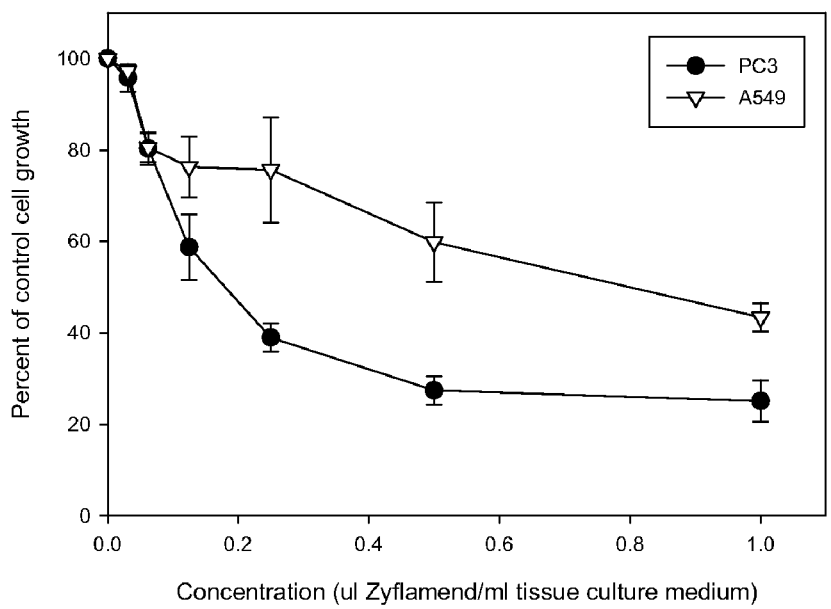
FIG. 1 is a graph depicting the inhibitory effect of the compositions of the present inventive subject matter on growth of human A549 lung cancer and human PC3 prostate cancer cell lines.

The term "modulating" refers to the process of producing an effect on biological activity, function, health, or condition of an organism in which such biological activity, function, health, or condition is maintained, enhanced, diminished, or treated in a manner which is consistent with the general health and well-being of the organism.

The term "enhancing" the biological activity, function, health, or condition of an organism refers to the process of augmenting, fortifying, strengthening, or improving.

The term "eicosanoid" refers to any of the class of compounds derived from polyunsaturated fatty acids, such as arachidonic acid and linolinic acid, and involved in cellular activity.

The term "oxygenase" refers to any of the class of enzymes that catalyze the incorporation of molecular oxygen into its substrate.

The term "supercritical gas" or "supercritical fluid" as used herein refers to a gas is that heated to a temperature critical point, over which the gas will maintain its gaseous state and not turn to a liquid regardless of pressure. A gas heated to a temperature above its critical point will become very dense on compression, so that its characteristics resemble those of a fluid, but will become liquid. Carbon dioxide is commonly used in applications requiring a supercritical fluid. The general properties of supercritical fluids and the general use of supercritical fluids in extraction processes are described in, e.g. Taylor, Supercritical Fluid Extraction, Wiley, 1996; McHugh and Krukonis, Supercritical Fluid Extraction: Principles and Practice, 2nd ed., Butterworth-Heinemann, 1994; and Williams and Clifford, Supercritical Fluid Methods and Protocols, Humana Press, 2000, the contents of which are incorporated by reference herein.

Applicants have developed a mixture comprised of herbal extracts, and the mixture has COX-2 inhibitory activity. Applicants' compositions are unique, in that some components of the composition are prepared via a supercritical $CO_2$ extraction process. Unlike traditional solvent based extraction methods, supercritical $CO_2$ extraction allows the natural products in the herbs to be obtained without leaving chemical residues behind in the preparation.

The term "supercritical extraction" as used herein refers to the technique in which hydrophobic compounds can be extracted from samples utilizing a supercritical fluid. The solvation power of a supercritical fluid is increased as the pressure and temperature are increased above their critical points, producing an effective solvent for the isolation of hydrophobic molecules. The term "supercritical extracts" refers to extracts prepared by supercritical extraction.

The term "hydroalcoholic extraction" as used herein refers to the technique in which hydrophilic compounds can be extracted from a sample utilizing a solution of alcohol and water, followed by evaporation of the solution to produce a extract consisting of dissolved solids. The term "hydroalcoholic extracts" refers to extracts prepared by hydroalcoholic extraction.

The term "13-S-HODE" refers to 13-hydroxyoctadeca-9Z, 11E-dienoic acid.

The term "NF-κB" or "nuclear factor kappa B" refers to a multisubunit transcription factor involved in gene expression. Active NF-κB consists of a dimer of a REL family/p65 subunit and a p50 or p52 subunit. NF-B is maintained in the cytoplasm through interactions with its inhibitor IκB, but upon dissociation translocates into the nucleus.

The Inventive Compositions

The inventive compositions are a genus of polyherbal preparations comprising constituents which exhibit anti-proliferative, anti-inflammatory, antioxidant, anti-angiogenic, and apoptotic activities. The inventive compositions are comprised of therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In one aspect, the active composition comprises:

(A) from about 4.5% to about 7.5%, and more preferably from about 5.5% to about 6.5%, by weight of the hydroalcoholic extract of ginger;

(B) from about 5.5% to about 8.5%, and more preferably from about 6% to about 8%, by weight of the supercritical extract of ginger;

(C) from about 1.0% to about 1.5%, and more preferably from about 1.2% to about 1.4%, by weight of the supercritical extract of turmeric;

(D) from about 10.0% to about 16.0%, and more preferably from about 11.5% to about 14.5%, by weight of the supercritical extract of rosemary;

(E) from about 4.0% to about 6.0%, and more preferably from about 4.5% to about 5.5%, by weight of the supercritical extract of oregano;

(F) from about 10.0% to about 16.0%, and more preferably from about 11.5% to about 14.5%, by weight of the hydroalcoholic extract of turmeric;

(G) from about 5.5% to about 8.0%, and more preferably from about 6.0% to about 7.0%, by weight of the hydroalcoholic extract of rosemary;

(H) from about 10.0% to about 16.0%, and more preferably from about 11.5% to about 14.5%, by weight of the hydroalcoholic extract of holy basil;

(I) from about 10.0% to about 16.0%, and more preferably from about 11.5% to about 14.5%, by weight of the hydroalcoholic extract of green tea;

(J) from about 8.0% to about 12.0%, and more preferably from about 9.0% to about 11.0%, by weight of the hydroalcoholic extract of huzhang;

(K) from about 4.0% to about 6.0%, and more preferably from about 4.5% to about 5.5%, by weight of the hydroalcoholic extract of Chinese goldthread;

(L) from about 4.0% to about 6.0%, and more preferably from about 4.5% to about 5.5%, by weight of the hydroalcoholic extract of barberry; and (M) from about 2.0% to about 3.0%, and more preferably from about 2.25% to about 2.75%, by weight of the hydroalcoholic extract of *Scutellaria baicalensis*.

Optionally, the hydroalcoholic extract of ginger, rosemary, turmeric, or oregano used in the present invention is preferably prepared as follows. The plant or a part thereof, which is preferably cryogenically ground to preserve heat sensitive components, is subjected to supercritical extraction, preferably with carbon dioxide, to obtain an oil extract, referred to herein as "the supercritical extract". In an additional optional embodiment, an oil-free residue is isolated from the first step and is then extracted in a water/alcohol, preferably water/ethanol, mixture composed of 60-80 parts alcohol and 40-20 parts water. The alcohol/water liquid is then evaporated off, leaving a powdered extract residue, referred to herein as "the hydroalcoholic extract".

Supercritical extracts of ginger, rosemary, turmeric and oregano optionally used in the present invention can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

In a preferred aspect, the weight ratio of the supercritical extract of ginger to the hydroalcoholic extract of ginger is from about 0.8:1 to about 1.4:1.

The hydroalcoholic extracts of rosemary, turmeric, holy basil, green tea, huzhang, Chinese goldthread, barberry and *Scutellaria baicalensis* used in the present invention can be prepared according to conventional hydroalcoholic extraction techniques. For example, the hydroalcoholic extracts can be prepared by extracting the plant portion in a water/alcohol, preferably water/ethanol, mixture preferably composed of 60-80 parts alcohol and 40-20 parts water, and then evaporating off the water/alcohol liquid, leaving a powdered extract residue referred to herein as "the hydroalcoholic extract".

In yet another aspect, the weight ratio of the hydroalcoholic extract of turmeric to the supercritical extract of turmeric is from about 8:1 to about 12:1.

In an alternate aspect, the weight ratio of the supercritical extract of rosemary to the hydroalcoholic extract of rosemary is from about 1.6:1 to about 2.4:1.

In a still further aspect, the hydroalcoholic extract of ginger comprises from about 2.4% to about 3.6%, more preferably from about 2.7% to about 3.3%, and most preferably about 3.0%, by weight of pungent compounds.

In another aspect, the supercritical extract of ginger comprises from about 24% to about 36%, more preferably from about 27% to about 33%, and most preferably about 30%, by weight of pungent compounds; and from about 6.4% to about 9.6%, more preferably from about 7.2% to about 8.8%, and most preferably about 8%, by weight of zingiberene.

In a further aspect, the supercritical extract of turmeric comprises from about 36% to about 54%, more preferably from about 40.5% to about 49.5%, and most preferably about 45%, by weight of turmerones.

In another aspect, the supercritical extract of rosemary comprises from about 18.4% to about 27.6%, more preferably from about 20.7% to about 25.3%, and most preferably about 23%, by weight of total phenolic antioxidants.

In yet another aspect, the supercritical extract of oregano comprises greater than about 4.0%, more preferably from about 4.5% to about 5.5%, and most preferably about 5.0%, by weight of total phenolic antioxidants.

In a still further aspect, the hydroalcoholic extract of turmeric comprises from about 5.6% to about 8.4%, more preferably from about 6.3% to about 7.7%, and most preferably about 7%, by weight of curcumin.

In another aspect, the hydroalcoholic extract of rosemary comprises from about 18.4% to about 27.6%, more preferably from about 20.7% to about 25.3%, and most preferably about 23%, by weight of total phenolic antioxidants.

In a further embodiment, the hydroalcoholic extract of holy basil comprises from about 1.6% to about 2.4%, more preferably from about 1.8% to about 2.2%, and most preferably about 2%, by weight of ursolic acid.

In a further aspect, the hydroalcoholic extract of green tea comprises from about 36% to about 54%, more preferably from about 40.5% to about 49.5%, and most preferably about 45%, by weight of polyphenols.

In another aspect, the hydroalcoholic extract of huzhang comprises from about 6.4% to about 9.6%, more preferably from about 7.2% to about 8.8%, and most preferably about 8%, by weight of reservatrols.

In another embodiment, the hydroalcoholic extract of Chinese goldthread comprises from about 4.8% to about 7.2%, more preferably from about 5.4% to about 6.6%, and most preferably about 6%, by weight of berberine.

In a further aspect, the hydroalcoholic extract of barberry comprises from about 4.8% to about 7.2%, more preferably from about 5.4% to about 6.6%, and most preferably about 6%, by weight of berberine.

In an alternate aspect, said composition comprises:

(A) from about 4.5% to about 7.5% by weight of the hydroalcoholic extract of ginger, wherein the extract comprises from about 2.4% to about 3.6% by weight of pungent compounds;

(B) from about 5.5% to about 8.5% by weight of the supercritical extract of ginger, wherein the extract comprises from about 24% to about 36% by weight of pungent compounds and from about 6.4% to about 9.6% by weight of zingiberene;

(C) from about 1.0% to about 1.5% by weight of the supercritical extract of turmeric, wherein the extract comprises from about 36% to about 54% by weight of turmerones;

(D) from about 10.0% to about 16.0% by weight of the supercritical extract of rosemary, wherein the extract comprises from about 18.4% to about 27.6% by weight of total phenolic antioxidants;

(E) from about 4.0% to about 6.0% by weight of the supercritical extract of oregano, wherein the extract comprises greater than about 4.0% by weight of total phenolic antioxidants;

(F) from about 10.0% to about 16.0% by weight of the hydroalcoholic extract of turmeric, wherein the extract comprises from about 5.6% to about 8.4% by weight of curcumin;

(G) from about 5.5% to about 8.0% by weight of the hydroalcoholic extract of rosemary, wherein the extract comprises from about 18.4% to about 27.6% by weight of total phenolic antioxidants;

(H) from about 10.0% to about 16.0% by weight of the hydroalcoholic extract of holy basil, wherein the extract comprises from about 1.6% to about 2.4% by weight of ursolic acid;

(I) from about 10.0% to about 16.0% by weight of the hydroalcoholic extract of green tea, wherein the extract comprises from about 36% to about 54% by weight of polyphenols;

(J) from about 8.0% to about 12.0% by weight of the hydroalcoholic extract of huzhang, wherein the extract comprises from about 6.4% to about 9.6% by weight of reservatrols;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of *Scutellaria baicalensis*;

and wherein said composition further comprises:

(i) the supercritical extract of ginger and the hydroalcoholic extract of ginger at a weight ratio of from about 0.8 to about 1.4 parts of supercritical extract per 1 part of hydroalcoholic extract;

(ii) the hydroalcoholic extract of turmeric and the supercritical extract of turmeric at a weight ratio of from about 8 to about 12 parts of hydroalcoholic extract per 1 part of supercritical extract; and (iii) the supercritical extract of rosemary and the hydroalcoholic extract of rosemary at a weight ratio of from about 1.6 to about 2.4 parts of supercritical extract per 1 part of hydroalcoholic extract.

In an alternate aspect, the composition comprises an additional agent selected from the group consisting of antineoplastic agents, growth inhibiting agents, and nutrients.

Set forth in Table 1 is a preferred embodiment of the orally administered composition, excluding inactive ingredients, as used in the inventive methods. The amounts recited in Table 1 represent the preferred dosage of the ingredients listed.

TABLE 1

| Herb | Type Of Extract | Plant Part | Amount (mg) |
| --- | --- | --- | --- |
| Rosemary | supercritical | leaf | 100 |
| Rosemary | hydroalcoholic (23% TPA 34.5 mg) | leaf | 50 |
| Turmeric | supercritical (45% turmerones 4.5 mg) | rhizome | 10 |
| Turmeric | hydroalcoholic (7% curcumin 7 mg) | rhizome | 100 |
| Ginger | supercritical (30% pungent compounds 16.2 mg 8% zingiberene) | rhizome | 54 |
| Ginger | hydroalcoholic (3% pungent compounds) | rhizome | 46 |
| Holy basil | hydroalcoholic (2% ursolic acid 2 mg) | leaf | 100 |
| Green tea | hydroalcoholic (45% polyphenols 45 mg) | leaf | 100 |
| Huzhang | hydroalcoholic (8% reservatrols 6.4 mg) | root & rhizome | 80 |
| Chinese Goldthread | hydroalcoholic (6% berberine) | root | 40 |
| Barberry | hydroalcoholic (6% berberine 2.4 mg) | root | 40 |
| Oregano | supercritical (≧4.0% TPA 1.8 mg) | leaf | 40 |
| *Scutellaria Baicalensis* | hydroalcoholic (5:1) | root | 20 |

Preferably, the composition set forth in Table 1 also includes extra virgin olive oil and yellow beeswax.

Methods of the Inventive Subject Matter

The compositions of the present inventive subject matter generally comprise standardized supercritical $CO_2$ concentrated extracts from plant products (ginger, rosemary, tumeric root, holy basil, green tea, huzhang, Chinese goldthread, barberry, oregano, and Baikal skullcap) typically consumed in an Eastern diet.

The inventive compositions were investigated for their anti-proliferative effects on human PC3 cells, and specifically analyzed for their effects on eicosanoid metabolism in this prostate cancer cell line. The inventive compositions were observed to produce a concentration-dependent inhibition of cloned COX-1, COX-2 and 5-LOX activities, with inhibition of production of 5-HETE being greater than that of PGE2 formation.

Applied to intact PC3 cells, the inventive compositions were found to be most potent against 12-LOX, followed by 5-LOX and then COX activities. Surprisingly, the appearance of 13-S-HODE in the PC3 cells was due to the presence of this eicosanoid in the inventive composition itself, and not to a stimulation of 15-LOX activity within the cells. The concentration dependent inhibition of proliferation of PC3 cells was associated with a selective G2/M arrest of the cell cycle and induction of apoptosis as evidenced by flow cytometry staining of PC3 cells with annexin V and phosphatidyl inositol.

The inventive compositions also produced a concentration-dependent down-regulation of 5-LOX and 12-LOX expression, although at high concentrations an up-regulation of COX-2 expression was noted. The phosphorylation status of several cell signal transduction proteins was determined. The inventive compositions produced an increase in p21 phosphorylation but down regulated phosphorylation of Rb and STAT1 proteins. The decrease in pRb proteins was shown to be due to 12-LOX inhibition and a decline in 12-HETE levels in the cells. Addition of 12-HETE back to the inventive compositions treated cells overcame the ability of the inventive compositions to inhibit cell proliferation and concordantly 12-HETE blocked the inventive compositions' ability to down-regulate phosphorylation of Rb protein.

It is concluded that the effective control of human prostate cancer cell proliferation with the inventive compositions is multi-mechanistic but in part involves regulation of aberrant tumor cell eicosanoid metabolism such as 12-LOX, application of plant-derived eicosanoid products such as 13-(S)-HODE as well as restoration of Rb tumor suppressor protein function through regulation of its phosphorylation status.

Further, other experiments demonstrated that while the compositions have shown potent inhibition of cyclooxygenase (cloned COX-1 and COX-2) activities, the ability to reduce growth of human prostate tumor cell growth produced by this product is believed to be in large part due to COX-2 independent mechanisms. Using a LC/MS/MS based method that simultaneously determines multiple eicosanoids in cells and tissues, changes in eicosanoid metabolism in cells and tissues produced by this unique herbal composition were examined.

Endogenous levels of intracellular PGE2, 12-HETE as well as 5-HETE declined in a concentration-dependent manner upon exposure to the compositions. In contrast, cellular levels of 15-HETE and 13-HODE were elevated. The elevation of 13-HODE was dramatic but, as discussed above, was due to a high content of 13-HODE present in the herbal composition itself and was not dependent on cellular generation of this important eicosanoid. The 13-HODE levels were considered to be high enough to account for inhibition of tumor cell growth that was independently verified by addition of authentic 13-HODE to tumor cell cultures.

Exposure of human tumor cells (PC3 prostate cancer cells) to the inventive composition also resulted in the downregulation of 5-LOX expression as determined by Western blot analyses. The ability of the inventive composition to block arachidonic acid mediated mouse ear inflammation was also assessed. The inventive compositions produced significant inhibition of LTB4 synthesis and up-regulated the production of 15-HETE.

Thus, the inventive subject matter relates to a method for modulating an eicosanoid metabolic process in cells of an animal in need thereof, which comprises administering to the animal an amount of a composition effective for regulating the activity of an eicosanoid oxygenase,
wherein the composition comprises therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In one aspect of the inventive subject matter, the cells are cancer cells. In one embodiment, the cancer cells comprise prostate cancer cells, breast cancer cells, lung cancer cells, colon cancer cells, or a combination thereof.

In an alternate embodiment, the eicosanoid metabolic process is aberrant metabolism associated with cellular transformation to cancer, cancer cell proliferation, cancer cell metastasis, cancer cell invasiveness, cancer cell-modulated angiogenesis, cancer cell-modulated apoptosis suppression, or a combination thereof.

Eicosanoid Metabolism. Arachidonic acid and its precursor, linoleic acid, along with linolinic acid, are present in animal fats and a variety of vegetable oils which are generally thought to be consumed in greater quantities in the typical Western diet in comparison to Eastern diets. The elevated intake of these fatty acids provides increased substrate availability for oxygenases such as lipoxygenases (LOX) and cyclooxygenases (COX), enzymes which are responsible for converting eicosanoids such as arachidonic acid into signaling molecules such as prostaglandins, leukotrienes, lipoxins, 13-S-HODE, 5-HETE, and 12-HETE. In addition to their vital role as second messengers in many important biological pathways, these products of eicosanoid metabolism have been implicated in all aspects of tumor development, progression, proliferation, and metastasis.

Lipoxygenases and Eicosanoid Metabolism. Lipoxygenase enzymes (LOXs) are known to be key regulators of cell survival and apoptosis in cells. They constitute a heterogeneous family of lipid peroxidizing enzymes that are categorized with respect to their regional specificity of arachidonic acid oxygenation. LOXs have been designated as 5-, 8-, 12-, and 15-LOX isoforms, which produce end products known as 5(S)-, 8(S)-, 12(S)-, and 15(S)-HETEs. Application of LC/MS/MS analyses of COX and LOX metabolism in PC3 cells was undertaken using a previously published technique. The results showed that the inventive compositions were, as expected, an inhibitor of both COX-1 and COX-2 cloned enzyme activity. In addition, it also inhibited cloned 5-LOX activity and, in fact was more potent as a 5-LOX inhibitor than as a COX inhibitor. Treatment of PC3 cells in culture showed that the inventive composition's ability to inhibit PGE2 formation through inhibition of COX was less than its ability to inhibit 5-LOX and this, in turn was less than the inventive composition-mediated inhibition of 12-LOX, an enzyme know to be important in proliferation and metastases of human prostate cancer.

12-HETE. Several lines of evidence now clearly implicate 12-LOX as a regulator of cancer cell development. The laboratory of K. Honn, in particular, has contributed greatly to the understanding of the role of platelet type 12-LOX and its product 12(S)—HETE in human prostate cancer. They reported, for example, that 12-LOX is expressed in several prostate cancer cells lines, that inhibitors of 12-LOX such as baicalein or BHPP significantly inhibit prostate tumor metastases and that 12-LOX levels are correlated with the grade and severity of human prostate tumors. A recent elegant report from this group has also shown that baicalein inhibition of prostate cell growth and proliferation is associated specifically with 12-LOX inhibition and that the decline in 12-HETE correlates with a loss of phosphorylated Rb proteins. The decreased phosphorylation of RB, in turn, results in RB protein remaining bound to transcription factors required for DNA synthesis and thus results in inhibition of cancer cell proliferation.

There are many bioactive lipids involved in inflammation associated with cancers such as early stage prostate cancer. These include the well documented ability of $PGE_2$ to stimulate tumor cell proliferation. This typically occurs through an over-expression of COX-2 in tumors as well the more recent finding of a decrease in PGDH activity, the enzyme responsible for metabolism of $PGE_2$. Lipoxygenase products such as 5-HETE from 5-lipoxygenase and 12-HETE from 12-lipoxygenase have also been shown to specifically drive prostate tumor cell proliferation. Because 12-HETE has been shown to be associated with prostate cancer proliferation, metastases and angiogenesis the suggestion that inhibition of 12-LOX represents a potential therapeutic approach in treatment of prostate cancer has recently been made. Other eicosanoids such as 13-S-HODE, the product of 15-LOX-1 and 15-HETE, the product of 15-LOX-2 appear to play opposing effects on signaling in cancers, especially prostate cancer, and may, in fact, be tumor type selective in their effects.

To better understand the role of selected bioactive eicosanoids in the progression of tissue inflammation towards malignant disease, Applicants have undertaken examination of prostate cell related inflammation profiles using an electrospray tandem mass spectrometry assay that Applicants developed. This method permits determination of "mini-lipidomics" in cell or tissue samples through simultaneous analyses of up to 10 cyclooxygenase, lipoxygenase and/or cytochrome P450 derived eicosanoids at one time without the need for addition of exogenous substrates such as arachidonic acid or linoleic acid.

To better understand the role of eicosanoids in human cancer Applicants used this novel tissue inflammation assay in PC3 cells to determine the effect of the inventive compositions on cyclooxygenase and lipoxygenase derived eicosanoids believed to be importance in proliferation of this human disease. Applicants have determined what effects, if any, the inventive compositions produced in eicosanoid metabolism beyond inhibition of cyclooxygenase activity. Our data suggest that this multiherb product inhibits 5-LOX and 12-LOX activities. The later finding may be of special interest in that suppression of 12-LOX activity was found to be associated specifically with inhibition of tumor cell proliferation and Rb phosphorylation, and thus return of tumor suppressor activity to hormone refractory PC3 prostate tumor cells.

Thus, in a preferred embodiment, the eicosanoid is selected from the group consisting of arachidonic acid and linolinic acid.

In a more preferred embodiment, the eicosanoid is arachidonic acid.

In a further aspect of the inventive subject matter, the eicosanoid oxygenase is cyclooxygenase-1, cyclooxygenase-2, 5-lipoxygenase, 12-lipoxygenase, or a combination thereof.

In a preferred embodiment, the eicosanoid oxygenase is 12-lipoxygenase.

In another preferred embodiment, the eicosanoid oxygenase is 5-lipoxygenase.

Cyclooxygenases. The cyclooxygenase enzymes that mediate eicosanoid metabolism are represented by two species, cyclooxygenase-1 (COX-1) which is constitutively expressed in many tissues and cyclooxygenase-2 (COX-2) which is typically induced during disease states such as inflammation and cancer. Data from many molecular and cellular biology studies have also suggested that the COX-2 gene is an early growth response gene affecting pathways that modulate apoptosis, proliferation, adhesion, angiogenesis and differentiation.

COX and especially COX-2 inhibition has been a main target for anti-inflammatory drug design for many years, however, the link between COX-2 expression and cancer has only been more recently recognized. Observations from several population-based studies have documented a significant decrease in the risk of colorectal cancer in people who regularly take non-steroidal anti-inflammatory drugs that have potent COX inhibitory activity. Histological studies that followed colorectal tumor development have determined that most human and animal colorectal tumors express elevated COX-2 levels, while adjacent normal colorectal epithelial cells have low to undetectable COX-2 levels. Similar to these observations, several laboratories have also reported that COX-2 expression is elevated in prostate tumor cells during both initiation and progression compared to normal epithelial cells, however this finding is controversial.

It is clear though, that several pharmacological COX-2 inhibitory drugs have shown the ability to suppress prostate cancer cell growth in vitro, induce apoptosis, and suppress growth of human prostate tumor xenografts in immunodeficient mouse models or transgenic models of prostate cancer such as the TRAMP mouse. Given the controversy as to whether COX-2 is a factor in prostate cancer development or progression, several of the known COX inhibitors are thought to have a variety of COX-independent anti-cancer effects and these actions appear to differ amongst inhibitors.

In this regard, it is very interesting that many plants which are prominent in regional diets contain substances that have COX inhibitory activity. Extracts from these plants, both in the crude form and as isolated components, have been found to have potent anti-inflammatory and anti-cancer activities. Salicylic acid, for example, is a traditional inflammatory inhibitor agent found in willow tree bark and the chemical derivative of this agent, aspirin, remains one of the most commonly used COX inhibitory substances in the world. In this study, Applicants considered the potential of a unique commercially available herbal preparation, the inventive compositions, for their ability to affect COX-1 and COX-2 enzyme activities and influence the behavior of a commonly used human prostate cancer cell model system, LNCaP cells. As discussed in detail above, the inventive compositions are comprised of ten standardized herbal extracts, (rosemary, turmeric, ginger, holy basil, green tea, hu zhang, Chinese goldthread, barberry, oregano, and *Scutellaria baicalensis*). Each of these herbs has been shown to contain unique chemical constituents that influence COX activity or expression, and each has been studied for either anti-inflammatory or anti-cancer activity. This testing tends to focus on the predominant compound found in any given herb, however there is reason to believe that there may be additive benefit in the combination of multiple herbal/dietary agents for diseases such as cancer. The multiple and chemically diverse constituents present in the inventive composition, each of which is an integral component of the typical Asian diet, may be more effective against prostate cancer than any single herbal extract alone.

Thus, in an alternate aspect of the inventive subject matter, the eicosanoid oxygenase is cyclooxygenase-1, cyclooxygenase-2, or a combination thereof.

In a preferred embodiment, the eicosanoid oxygenase is cyclooxygenase-1.

In a further preferred embodiment, the eicosanoid oxygenase is cyclooxygenase-2.

In one alternative aspect of the inventive subject matter, the regulation of the activity of an eicosanoid oxygenase is oxygenase inhibition.

In an alternate aspect of the inventive subject matter, modulation of an eicosanoid metabolic process comprises inhibiting NF-κB activity in the cells of the animal.

The inventive subject matter further relates to a method of delivering 13-S-HODE to an animal in need thereof, comprising administering to the animal a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

Additionally, the inventive subject matter relates to a method for inhibiting arachidonic acid-mediated inflammation in an animal in need thereof, comprising administering to the animal a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

NF-κB. Nuclear factor κB is a family of Rel-domain containing proteins present in the cytoplasm of all cells, where they are kept in an inactive state by a family of anchorin-domain-containing proteins which includes IκBα, IκBβ, IκBγ, IκBε, bcl-3, p105 and p100. Under resting conditions, NF-κB consists of a heterotrimer of p50, p65, and IκBα in the cytoplasm; only when activated and translocated to the nucleus is the sequence of events leading to transcription initiated. Most carcinogens, inflammatory agents, and tumor promoters, including cigarette smoke condensate, phorbol ester, okadaic acid, $H_2O_2$, and tumor necrosis factor (TNF), have been shown to activate an NF-κB activation pathway. The activation of NF-κB involves the phosphorylation, ubiquitination, and degradation of IκBα and phosphorylation of p65, which in turn leads to the translocation of NF-κB to the cell nucleus, where it binds to specific response elements in the DNA. The phosphorylation of IκBα is catalyzed by IκBα kinase (IKK), which is essential for NF-κB activation by most agents. NF-κB has been shown to regulate the expression of a number of genes whose products are involved in tumorigenesis. These include antiapoptotic genes (e.g. ciap, suvivin, traf, cflip, bfl-1, bcl-2 and bcl-x1), angiogenesis (cox-2, mmp-9, vegf), genes encoding adhesion molecules, chemokines, and inflammatory cytokines; and cell cycle regulatory genes (e.g., cyclin d1, c-myc).

Without being bound to a particular mechanism of action, Applicants believe that the inventive compositions modulate the activity of the nuclear factor KB ("NF-κB"), which in turn regulates proliferation, invasion, and metastasis of tumor cells, inhibits feedback NF-κB activation, and regulates expression of NF-κB-regulated gene products. In particular, Applicants have found that the inventive compositions inhibit receptor activator of NF-κB ligand induced osteoclastogenesis, suppresses tumor necrosis factor (TNF)-induced invasion, and potentiates the apoptosis induced by TNF and chemotherapeutic agents. Further, the inventive compositions suppresses NF-κB activation induced by both TNF and cigarette smoke condensate. In addition, the inventive compositions downregulates the expression of NF-κB-regulated gene products involved in anti-apoptosis, including inhibitor-of-apoptosis protein 1/2, Bcl-2, Bcl-xL, FADD like interleukin-1β converting enzyme (FLICE)/caspase-8 inhibitory protein, TNF receptor-associated factor 1, and survivin, and further downregulates the expression of gene products involved in angiogenesis, including vascular endothelial growth factor, cyclooxygenase-2, intercellular adhesion molecule, and matrix metalloproteinase. These results correlate with potentiation of apoptosis induced by TNF and chemotherapeutic agents. Overall Applicants' results indicate that the inventive compositions suppress osteoclastogenesis, inhibits invasion, and potentiates apoptosis through downregulation of NF-κB activation and downregulation of NF-κB-regulated gene products.

Applicants have determined some of the effects of the inventive compositions on the NF-κB activation pathway and on the NF-κB-regulated gene products which control tumor cell survival, proliferation, invasion, angiogenesis, and metastasis, finding that the inventive compositions inhibits RANKL-induced osteoclastogenesis and TNF-induced invasion, and potentiates apoptosis induced by TNF and chemotherapeutic agents in various tumor cell lines. The expression of gene products involved in anti-apoptosis, including IAP1, Bfl-1/A1, Bcl-2, TRAF1, and cFLIP, and expression of gene products involved in metastasis, including MMP-9, COX-2, ICAM-1, and VEGF, were also downregulated by the inventive compositions.

Applicants' data indicate that the inventive compositions suppress NF-κB activated by TNF in human myeloid leukemia KBM-5 cells and cigarette smoke condensate in lung adenocarcinoma H1299 cells. This is the first investigation to examine the effect of the inventive compositions on NF-κB activated by different stimuli. These results suggest that the inventive compositions act at a step common to both these agents. Several genes that are involved in the proliferation and metastasis of cancer have been shown to be regulated by NF-κB. (See, e.g., Aggarwal, B. B. (2004) Nuclear factor-kappa B: the enemy within. *Cancer Cell*, 6, 203-208.) Applicants have shown that the inventive compositions inhibit the expression of COX-2, MMP-9, and VEGF regulated by NF-κB.

Further, while recent reports have suggested that the inventive compositions suppress both COX-1 and COX-2 enzymatic activities (See, e.g., Bemis, D. L., Capodice, J. L., Anastasiadis, A. G., Katz, A. E. and Buttyan, R. (2005) Zyflamend, a unique herbal preparation with nonselective COX inhibitory activity, induces apoptosis of prostate cancer cells that lack COX-2 expression. *Nutr. Cancer.*, 52, 202-212), Applicants have shown that the inventive compositions inhibits the expression of the COX-2 protein.

Applicants' data suggest that the inventive compositions exercise its anti-cancer properties on NF-κB-regulated pathways through the direct inhibition of NF-κB. NF-κB is known to regulate the expression of IAP1, xIAP, Bfl-1/A1, TRAF1, Bcl-2, cFLIP, and survivin, and their overexpression in numerous tumors has been linked to survival, chemoresistance, and radioresistance. (See, e.g., Takada, Y., Singh, S. and Aggarwal, B. B. (2004) Identification of a p65 peptide that selectively inhibits NF-kappa B activation induced by various inflammatory stimuli and its role in down-regulation of NF-kappa B-mediated gene expression and up-regulation of apoptosis. *J. Biol. Chem.*, 279, 15096-15104.) Applicants' data indicate that the inventive compositions treatment downregulates most of these gene products. Previous reports have suggested that the inventive compositions induce apoptosis through a caspase-mediated pathway in human prostate cancer cells (See, e.g., Bemis, et al., (2005)). Applicants' results also show that the inventive compositions potentiate the apoptotic effects of TNF, taxol, and doxorubicin. These effects are similar to those that have been reported with a specific inhibitor of NF-κB (See, e.g., Takada, et al. (2004)).

Again without being bound to a particular mechanism of action, Applicants believe that antiproliferative, pro-apoptotic, anti-invasive, anti-osteoclastogenic, anti-angiogenic, and anti-metastatic effects observed upon administration of the inventive compositions are mediated through suppression of NF-κB-regulated gene products. Whereas each of the herbs that are used in the formulation of the inventive compositions are known to contain unique anti-inflammatory and anticancer compounds, one common property of the components of the inventive compositions appears to be the ability to suppress NF-κB activation.

Considering the fact that the inventive compositions is derived from natural herbal sources and is readily available in health food and nutritional supplement source, make it a more convenient and desirable means for prevention and treatment of cancer than prescription cancer drugs.

Thus, the inventive subject matter also relates to a method for modulating the level of NF-κB-regulated gene products in cells of an animal in need thereof, comprising administering to the animal a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

The animal in all of the inventive methods disclosed above may be a mammal such as a mouse, rat, cat, dog, horse, cow, or other domesticated animal, or a human. In a preferred embodiment, the animal is human. In addition to uses for treating human diseases, disorders, and conditions, the inventive methods may have veterinary applications.

Routes of Administration

In a preferred embodiment, an orally administered composition is in the form of one or more capsules, one or more tablets, or one or more pills.

The inventive compositions are preferably delivered to the patient by means of a pharmaceutically acceptable carrier. Such carriers are well known in the art and generally will be in either solid or liquid form. Solid form pharmaceutical preparations which may be prepared according to the inventive subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The inventive pharmaceutical preparations may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

The pharmaceutical preparation may also be prepared in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

It is not expected that compounds of the inventive subject matter will display significant adverse interactions with other synthetic or naturally occurring substances. Thus, a compound of the inventive subject matter may be administered in combination with other compounds and compositions useful, for example, for treating cancer. In particular the compounds of the inventive subject matter may be administered in combination with other compounds of the inventive subject matter, chemotherapeutic substances, and so forth.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the inventive subject matter.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the inventive subject matter may usually be given in two or three doses daily. Starting with a low dose (200-300 mg) twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the inventive subject matter and are not intended to be limitations thereon. Unless otherwise indicated, all percentages are based upon 100% by weight of the final composition.

General Materials and Methods

Zyflamend®, obtained from New Chapter Inc. (St. Louis, Mo.), was dissolved in dimethyl sulfoxide ("DMSO") as a 10 mg/ml stock solution and stored at −20° C. Bacteria-derived human tumor necrosis factor alpha ("TNF-α"), purified to homogeneity with a specific activity of $5 \times 10^7$ U/mg, was kindly provided by Genentech, Inc. (South San Francisco, Calif.). Penicillin, streptomycin, RPMI 1640 medium, Iscove's modified dulbecco medium ("IMDM"), D-MEM/F12 medium and fetal bovine serum ("FBS") were obtained from Invitrogen (Grand Island, N.Y.). The following polyclonal antibodies were obtained from Santa Cruz Biotechnology, Inc. (Santa Cruz, Calif.): anti-matrix metalloproteinase 9 ("MMP-9"); anti-intercellular adhesion molecule ("ICAM"); antiinhibitor-of-apoptosis protein 1/2 ("IAP 1/2"); anti-Bcl-2; anti-Bfl-1/A1; and anti-TNF receptor-associated factor ("TRAF1"). Anti-COX-2 and XIAP were obtained from BD Biosciences (San Diego, Calif.). Cigarette smoke condensate ("CSC"), prepared as described in Anto, R. J., Mukhopadhyay, A., Shishodia, S., Gairola, C. G. and Aggarwal, B. B. (2002) Cigarette smoke condensate activates nuclear transcription factor-kappa B through phosphorylation and degradation of I kappa B(alpha): correlation with induction of cyclooxygenase-2. Carcinogenesis, 23, 1511-1518, was kindly supplied by Dr. G. Gairola (University of Kentucky, Lexington, Ky.). An anti-vascular endothelial growth factor ("VEGF") was purchased from NeoMarkers (Fremont, Calif.). Survivin antibody was obtained from R&B Systems (Minneapolis, Minn.). An FADD-like interleukin-1β-converting enzyme ("FLICE")/caspase-8-inhibitory protein ("cFLIP") antibodies were kindly provided by Imgenex (San Diego, Calif.).

The cell lines used in Applicants' work include human non-small cell lung carcinoma (H1299), human myelogenous leukemia (KBM-5), and human multiple myeloma (U266), mouse macrophages (RAW 264.7) cell lines were obtained from the American Type Culture Collection (Manassas, Va.). H1299, and U266 cells were cultured in RPMI 1640 medium with 10% FBS. KBM-5 cells were cultured in IMDM with 15% FBS. RAW 264.7 cells were cultured in D-MEM/F12 medium supplemented with 10% FBS. All the media were supplemented with 100 U/ml penicillin and 100 μg/ml streptomycin.

Example 1

Inhibition of Cell Growth

As a general starting point, the relative ability of a product or drug to inhibit cell growth using established rodent and human cell lines in culture is investigated. The purpose of this is simply to be able to discern those concentrations that are either ineffective or toxic from those that are significantly inhibitory or "effective". Any exploration of mechanisms of action of a given product should be done at concentrations that produce some but not profound inhibition of growth or massive cell death. In addition, these kinds of studies provide an initial estimate of time-dependent changes in cell events. That is, when drug-mediated events occur relative to the first indications of growth inhibition or cell death is discernable. This, in turn, may suggest a sequence of events that are involved.

Most of the studies focused upon include using human prostate cancer cell lines. The reason for this includes the fact that this is a cell line of interest, the cell lines have been characterized by us for eicosanoid metabolism and Applicants are involved in an ongoing clinical trial of the inventive compositions in the treatment/prevention of PIN. However, as the data are obtained, use of other cell lines and animal models that have little to do with prostate cancer itself but are, instead, useful for understanding general anti-inflammatory activity and mechanisms might be used.

FIG. 1 shows the inhibitory effect of the inventive compounds on growth of human A549 lung cancer and human PC3 prostate cancer cell lines. The oral formulation of the composition was used. The composition was added to cells in culture and relative inhibition of cell growth was assessed after 72 hours of continuous exposure to drug. The "MTT" method was used to assess cell proliferation versus untreated control cell populations. The greater inhibition of the growth of prostate PC3 cells compared to that of lung adenocarcinoma cells is apparent.

Figure 8:
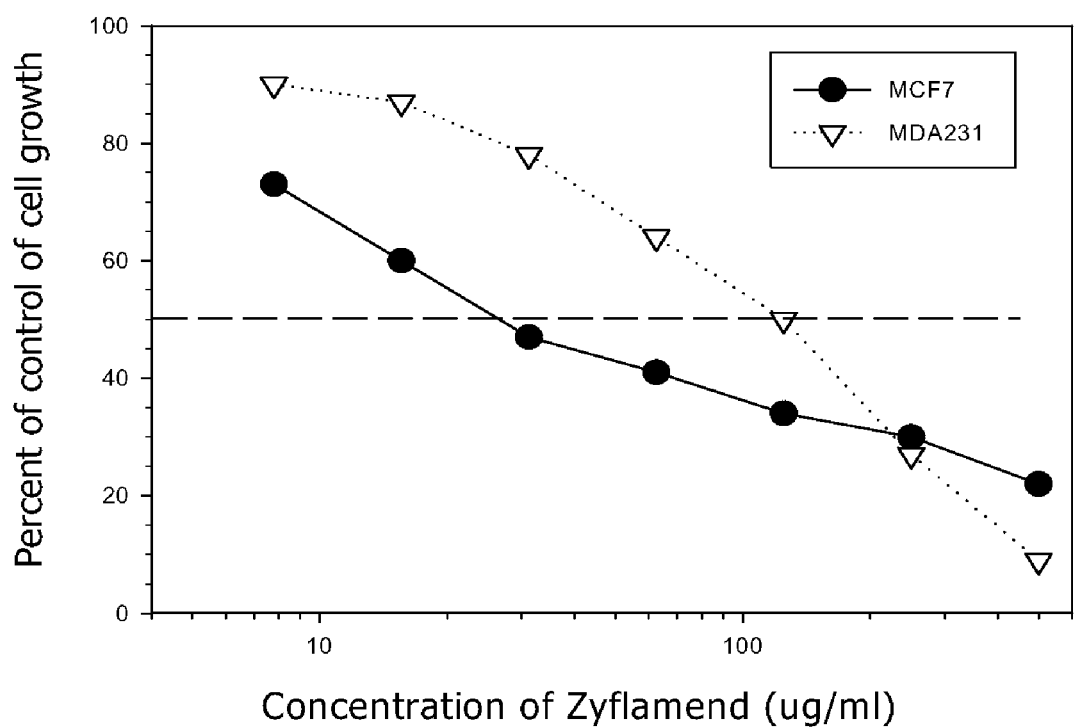
FIG. 8 is a graph depicting the inhibitory effect of the inventive compounds on growth of human breast cancer MCF7 and MDA231 cell lines.

Likewise, FIG. 8 and Table 2 depict the inhibitory effect of the compound on growth of human breast cancer MCF7 and MDA231 cell lines. Again, the oral formulation of the inventive compositions was used. The composition was added to cells in culture and relative inhibition of cell growth was assessed after 72 hours of continuous exposure to drug. The "MTT" method was used to assess cell proliferation versus untreated control cell populations. The MCF7 cells were more sensitive to the composition exposure than were the MDA231 cells.

TABLE 2

| Cell Line | *IC$_{50}$ |
|---|---|
| PC3 human prostate | 146 |
| Epi human normal epithelial | >1000 |
| MCF7 human breast cancer (estrogen sensitive) | 27 |
| MDA231 human breast cancer (estrogen refractory) | 126 |
| A549 human lung adenocarcinoma | 435 |

*The IC$_{50}$ is defined as that concentration (ug/ml) of material that produces inhibition of growth of cells by 50% (relative to untreated cells) under defined conditions (typically duration) of exposure to that agent.

The relative lack of cytotoxicity against the only "normal" human epithelial cell line tested is clearly of interest for purposes of patient tolerance of the medication and compliance with the administration protocol. The sensitivity of human breast MCF-7 estrogen sensitive cell line to the composition is of special interest, and this cell line is definitely the most sensitive one tested to date. Applicants are unaware of any compounds in the plant extracts used to make up the inventive composition which block estrogen binding, which Applicants believe rule out this alternate explanation for the observed high sensitivity.

Example 2

Ability of the Inventive Composition to Inhibit Cyclooxygenase (COX) and Lipoxygenase (LOX) Enzymes Applicants have determined the relative effect of the inventive compositions against COX-1, COX-2, and other eicosanoids of interest. These studies have indicated that the composition inhibits both COX-1 and COX-2 (as cloned enzymes), as Applicants expected based upon the varied anti-inflammatory components obtained from the different herbal extracts that comprise the inventive composition. The data also indicate that the composition is a useful inhibitor of 5-lipoxygenase (5-LOX) as well. No selective change in eicosanoid products derived from 15-LOX-2 was observed. The data also demonstrate that the compositions inhibit 12-lipoxygenase in a concentration-dependent manner. The data in FIGS. 2 and 3 indicate that the composition is potent in terms of producing inhibition of cloned COX enzymes as well as enzymes in cells in culture. Only small microliter amounts of the inventive composition in liquid were sufficient to produce a significant inhibition of cyclooxygenase enzymes. This is especially impressive when it is recalled that 60% of this particular formulation of the composition is olive oil, which itself has no effect on eicosanoid metabolism.

Figure 2:
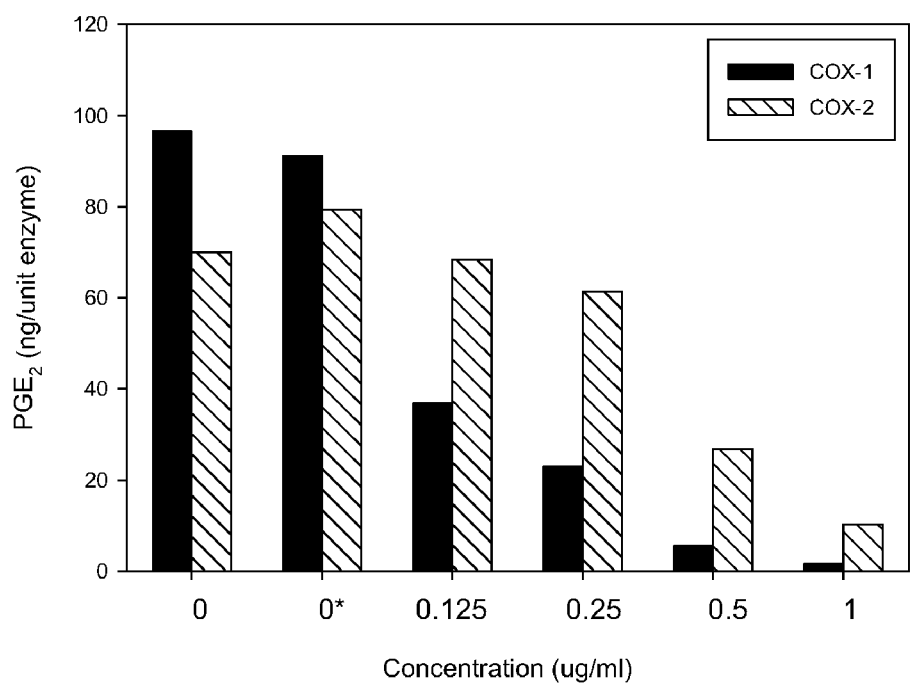
FIG. 2 is a graph depicting the effect of the inventive compositions on formation of PGE2.

FIG. 2 depicts the effect of the composition on formation of PGE2 using cloned COX-1 (ovine) and COX-2 (human) enzymes was measured by incubation of 10 uM AA with the enzymes (15 IU) in 0.1 M Tris-HCl buffer, pH 8.0, containing 5 mM EDTA, 2 mM phenol, and 1 uM hematin. Aliquots of the composition were added to tubes prior to addition of AA. Control incubations did not contain the composition. The bars with the asterisk represent the "olive oil" control. Incubations were carried out at 37° C. for 15 min. Reactions were stopped by addition of 1 N citric acid. Eicosanoids were then extracted using a hexane:ethyl acetate (1:1) solvent mixture; the extract was brought to dryness under nitrogen. PGE2 formed during the incubation was extracted as previously described and then analyzed using our published LC/MS/MS method (Yang et al. Anal Biochem. 308: 168-177, 2002). The data depicted in FIG. 2 suggest that the inventive composition inhibits the formation of PGE2 by both COX-1 and COX-2, although the product is more potent at inhibiting COX-1 than COX-2.

Figure 3:
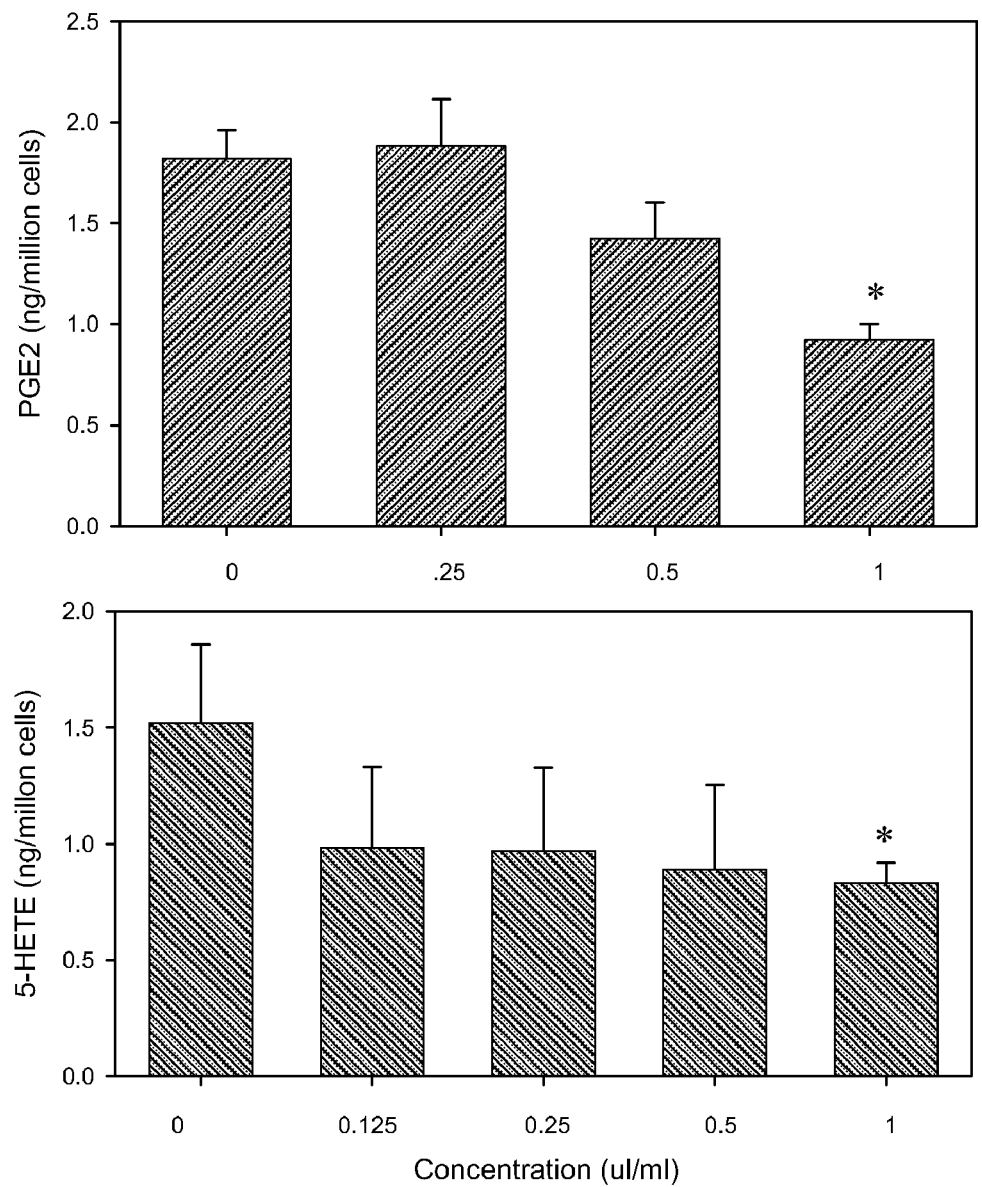
FIG. 3 is a graph depicting effect of the inventive compositions on formation of PGE2 and 5-HETE in PC3 cells.

FIG. 3 shows the effect of the composition on formation of PGE2 and 5-HETE in PC3 cells. Varying concentrations of the composition were added to cell cultures in fresh serum-free medium supplemented with 15 uM BSA and incubated at 37° C. for min. Arachidonic acid (100 uM) and cofactors were then added. After 10 min cells were washed and extracted to determine eicosanoid formed within the cells (see legend to FIG. 2). The data indicate a concentration-dependent inhibition of both PGE2 as well as 5-HETE in PC-3 cells. Data are presented as Mean±SD (n=3). * Indicates P<0.05 relative to controls.

Example 3

Effect of the Inventive Compositions on Cellular Expression of 5-Lipoxygenase

An anti-inflammatory agent can achieve its pharmacologic effect through many different mechanisms. A given product can inhibit selective enzymes involved with formation of inflammation related molecules, for example inhibition of COX-2 to decrease formation of PGE2 or inhibition of 5-lipoxygenase to decrease formation of 5-HETE. The compositions also inhibit activation transcription factors that are known to be directly involved in activation of inflammation related genes, such as curcumin-mediated inhibition of activation of NF-κB.

In addition, a given product may also act to decrease the actual synthesis, and therefore expression, of the enzyme in a cell or tissue, rather than directly inhibit it. The initial data we have obtained indicates that the inventive compositions provide a concentration-dependent inhibition of the relative expression of 5-lipoxygenase in cells in addition to its inhibition of enzyme activity. The relative inhibition of enzyme expression is not a general phenomenon, as the composition does not appear to inhibit the relative tissue expression of COX-2.

Example 4

Identification of 13-S-HODE in the Inventive Composition

Figure 4:
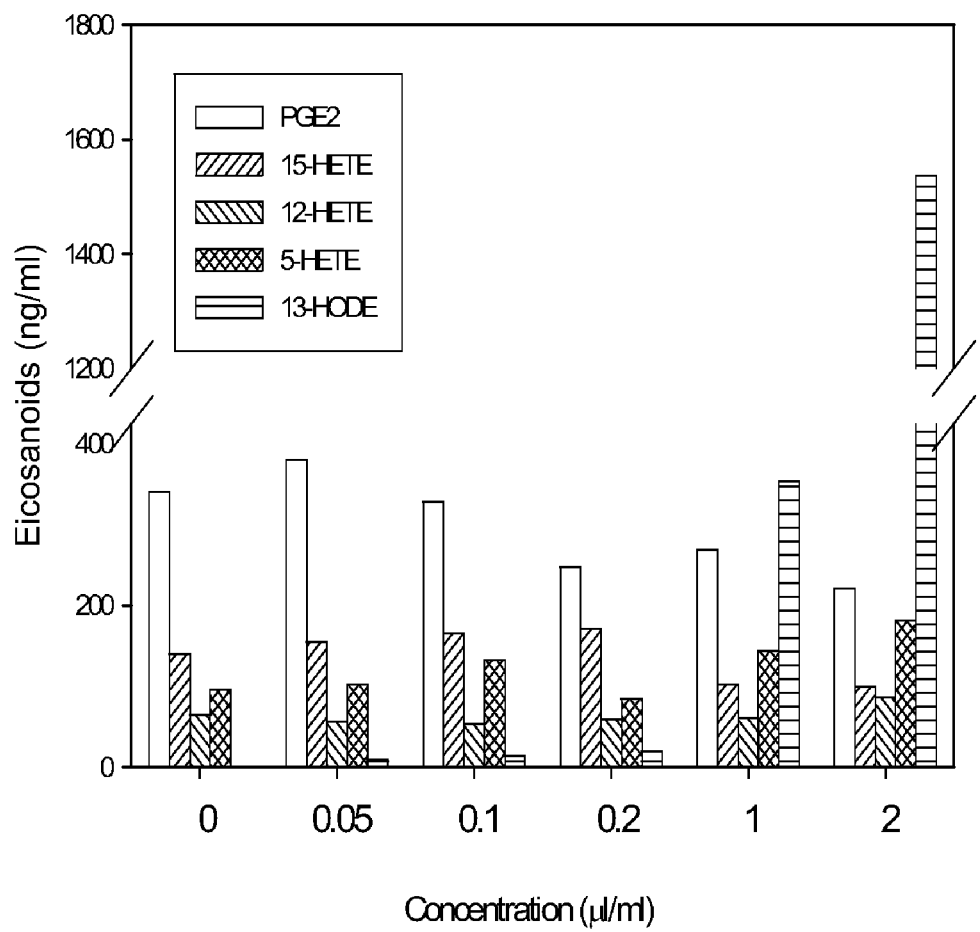
FIG. 4 is a graph depicting the concentration-dependent effect of the inventive compositions on eicosanoid metabolism in human A549 lung cancer cells.

FIG. 4 shows the Concentration-dependent effect of the inventive composition on eicosanoid metabolism in human A549 lung cancer cells, showing apparent concentration-dependent increase in formation of 13-S-HODE. Cells ($1\times10^6$) were allowed to attach overnight to the tissue culture plate and were then treated for 24 hours with different concentrations of the composition as shown in the Figure. Cells were then harvested and extracted for eicosanoid analyses by LC/MS/MS. The data indicate a small inhibition (32%) of PGE2 at a composition concentration of 2 ul/ml but also show an "apparent" dramatic formation of 13-S-HODE at 1 and 2 ul/ml.

The effect of the composition on conversion of arachidonic acid to various eicosanoid products in several cell lines was examined. The data shown above suggest that, at least for human lung A459 cells, the composition dose not have a large effect on cyclooxygenase or lipoxygenase enzymes. The concentration-dependent increase in 13-S-HODE, the product of 15-LOX-1 enzyme is, however, striking. Such an increase in 13-5-HODS can arise from either an induction of the enzyme itself, or enzyme activity, addition of a suitable substrate such as linoleic acid that would preferentially give rise to 13-S-HODE, or through another mechanism. Induction of 15-LOX-1 does, in fact, happen when NSAIDs are added to colon cancer cells and this serves as a partial explanation for the beneficial effect of aspirin as a preventive agent in colon cancer. However, by Western blot, no significant induction of 15-LOX-1 enzyme as a result of incubation with the composition was observed. The inventive composition was also examined for relative content of linoleic acid, a substrate that can give rise to 13-S-HODE through 15-LOX-1 enzyme. Using a GC/MS/MS instrument, only a minimal amount of linoleic acid was found. Examination of the composition itself, however, indicated the presence of a high amount of 13-S-HODE as discussed in Example 6 below.

Figure 5:
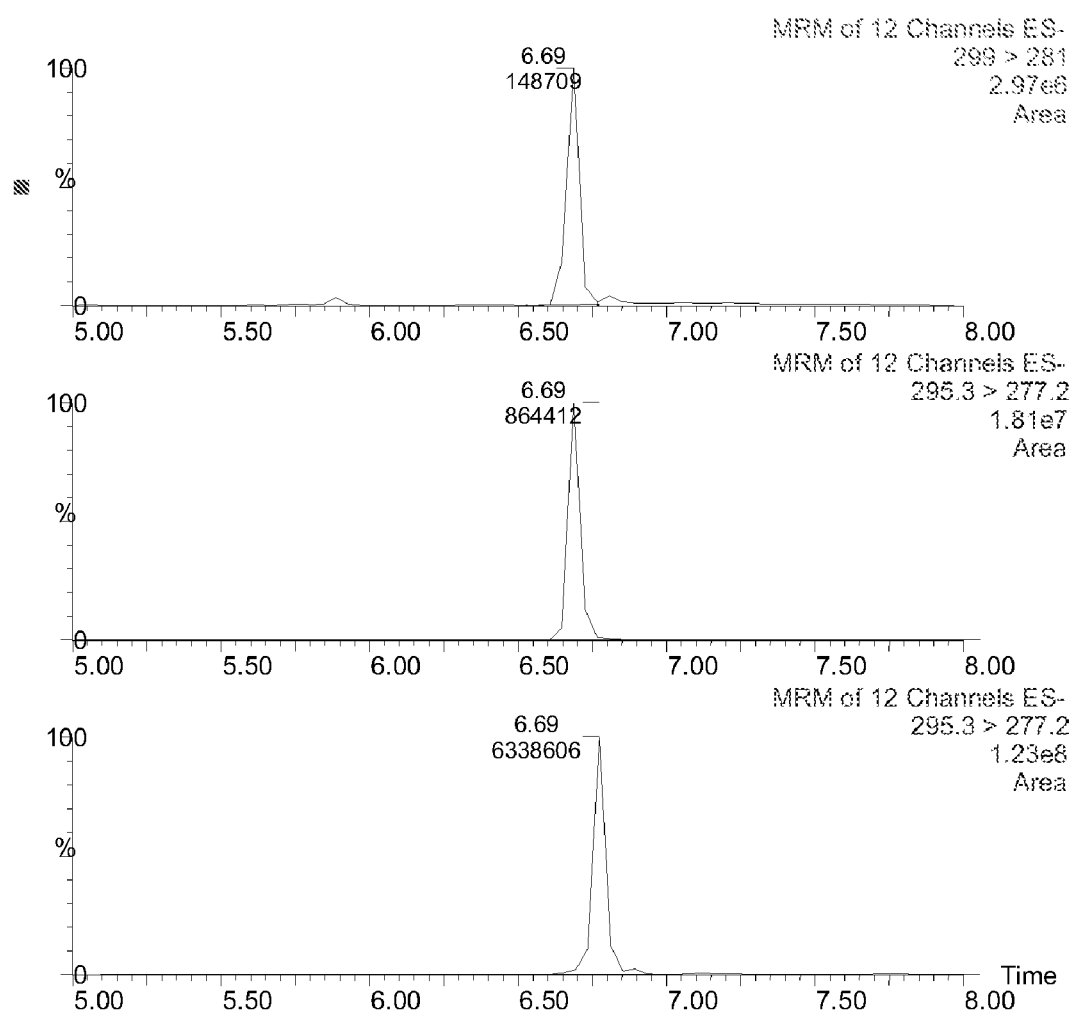
FIG. 5 shows mass spectra data showing presence of 13-S-HODE in the inventive compositions.

FIG. 5 shows mass spectra data showing presence of 13-S-HODS in the inventive compositions. FIG. 5 represents three plots of related information. The uppermost plot is a total ion chromatogram of deuterated 13-S-HODE (designated as 13-S-HODE-d4). The four deuterium atoms provide a higher molecular weight (addition of 4) to the mass weight of 13-S—HODE itself. The mass weight of the deuterated product (indicated by the mass to charge ratio on the upper right is "299". This is basically the mass weight of this product. The notation of 299>281 reflects the fact that Applicants have the instrument select for the mass weight of 299 and then collide the molecule with argon (an inert gas) to produce a characteristic "daughter" ion at 281. This daughter ion can be used for quantitative purposes.

The middle plot indicates the ion trace for authentic 13-S-HODE (25 ng/ml) purchased from Cayman Chemicals (Ann Arbor, Mich.). It has a mass weight of 295.3 and this is indicated in the plot. Applicants look at the daughter ion at 277.2 to characterize the compound. That is, the chances of any one given molecule having a mass weight of 277.2 that also "breaks" to produce a daughter ion of 277.2 is almost nil except for the actual molecule of interest: 13-S-HODE.

The bottom plot is an extract of the inventive composition. The mass spec was instructed to look for all molecules with a mass weight of 295.3. Applicants then set the instrument to look at only characteristic daughter ions at 277.2. The fact that the instrument found them ... in abundance ... indicates beyond a shadow of a doubt that 13-S-HODE is present in the inventive compositions. The extract was obtained from only 5 ul of the composition. The two numbers by each peak represent the retention time of the peak (e.g. 6.69 min) and the relative ion abundance. The later is analogous to the "amount" of product within the peak. The fact that an authentic standard of 13-S-HODE at 25 ng/ml provided a peak amount of 864,412 while only 5 ul of the composition produces a peak "amount" of 6,338,606 clearly indicates the high amount of this eicosanoid within the composition. What is important to know is that this is "take it to the bank" proof that the composition contains a lot of 13-S-HODE.

To assure that 13-S-HODE is the substance being dealt with, the presence of 13-S-HODE in the inventive composition was assayed using an antibody based Enzyme Immunoassay kit. The antibody provides the specificity for detecting 13-S-HODE. The EIA analyses confirmed the presence of a high amount of 13-S-HODE in the inventive compositions.

Figure 9:
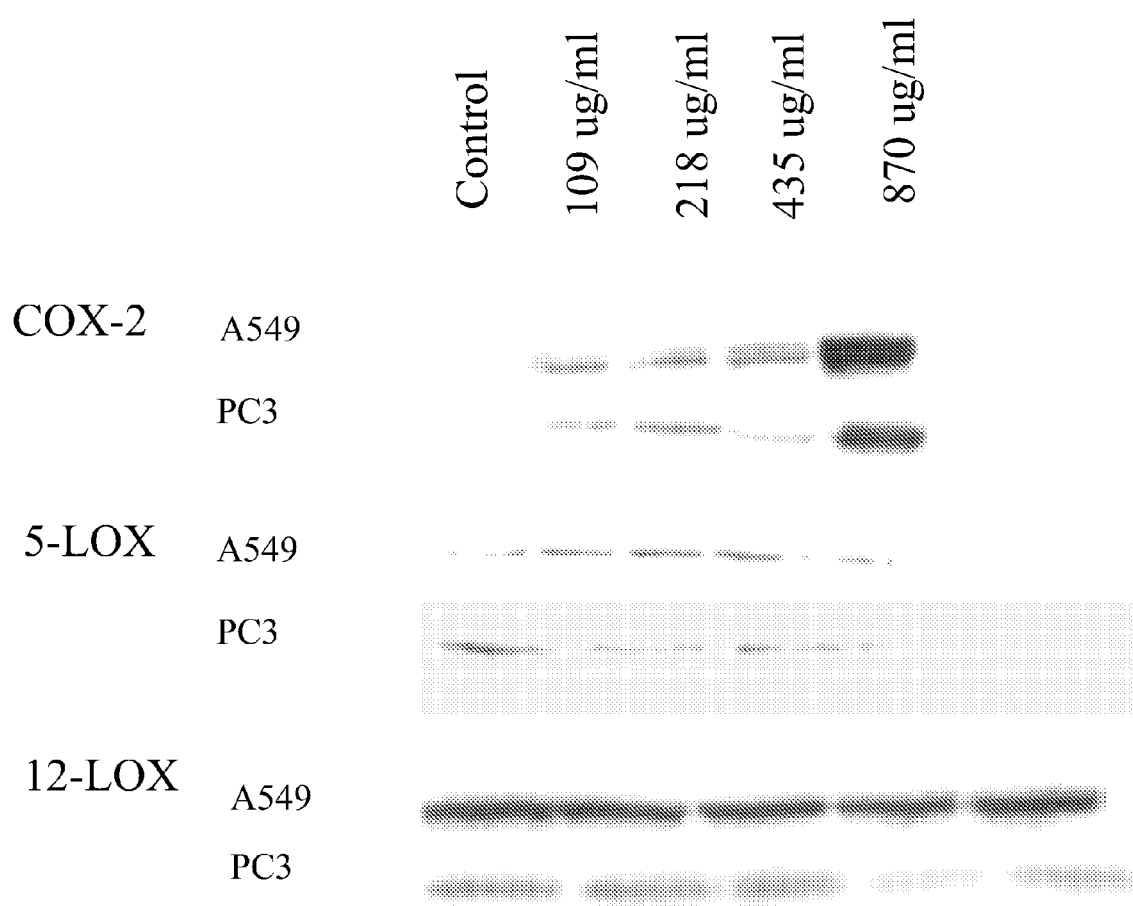
FIG. 9 is a Western blot depicting the ability of the inventive compositions to down-regulate in a concentration-dependent manner the presence of 5-lipoxygenase in human tumor cell lines (e.g. PC3).

An anti-inflammatory agent can achieve its pharmacologic effect through many different mechanisms. For example, a given product can inhibit selective enzymes involved with formation of inflammation related molecules (e.g. inhibition of COX-2 to decrease formation of $PGE_2$ or inhibition of 5-lipoxygenase to decrease formation of 5-HETE). The product could also inhibit activation transcription factors that are known to be directly involved in activation of inflammation related genes (e.g. curcumin mediated inhibition of activation of NF-θB). In addition, a given product may also act to decrease the actual synthesis and therefore expression of the enzyme in a cell or tissue rather than directly inhibit it. The initial data obtained indicates that the inventive composition can, in fact, lead to a concentration-dependent inhibition of the relative expression of 5-lipoxygenase in cells in addition to inhibition of enzyme activity. The relative inhibition of enzyme expression is not a general phenomenon as the composition does not appear to inhibit the relative tissue expression of 12-LOX. Nor is the disappearance (down-regulation) of expression of 5-LOX a general result of exposure to 5-LOX inhibitors to cells. Although not in this report, the relative effect of 5-LOX protein content (Western blot) after PC3 cells had been exposed to the established 5-LOX inhibitor Zileuton was examined. As shopwn in FIG. 9, while Zileuton is a potent 5-LOX inhibitor (and is useful for treatment of asthma because of this), it did not produce any change in relative 5-LOX enzyme content within cells.

One of the interesting things is the concentration dependent increase in COX-2 protein expression that occurs as a result of exposure of cells to the composition. At first glance this would appear to be exactly what Applicants would NOT want to happen. After all, inhibition of COX-2 is the foundation for a large pharmaceutical business. But, little recognized is the fact that Celebrex (celecoxib) is a known inducer of COX-2! Inflammation stays in check because enzyme activity is inhibited while Mother nature tries her best to overcome that with increased synthesis of the enzyme. In other words, people on COX-2 inhibitors do just fine . . . until they stop taking them.

Example 5

In Vivo Determination of Anti-Inflammatory Effect of the Inventive Compositions: Mouse Ear Model A very simple yet effective animal model of inflammation has been used for the past several years. The right ear of the test mouse is pretreated with a presumed anti-inflammatory agent then left alone for 30 minutes. An inflammatory agent (typically arachidonic acid (AA) in acetone) is then applied to that same ear. The vehicle is applied to the left ear as a control. A fixed period of time after application of AA, the mice is anesthetized and then a round ear punch is used to obtain a uniform segment of tissue. The difference in weight of tissue from each mouse ear punch serves as a relative index of the relative prevention of inflammation. After weighing, the ear punch sample is then rapidly frozen for subsequent analyses of specific eicosanoid metabolism through use of our LC/MS/MS method.

Figure 6:
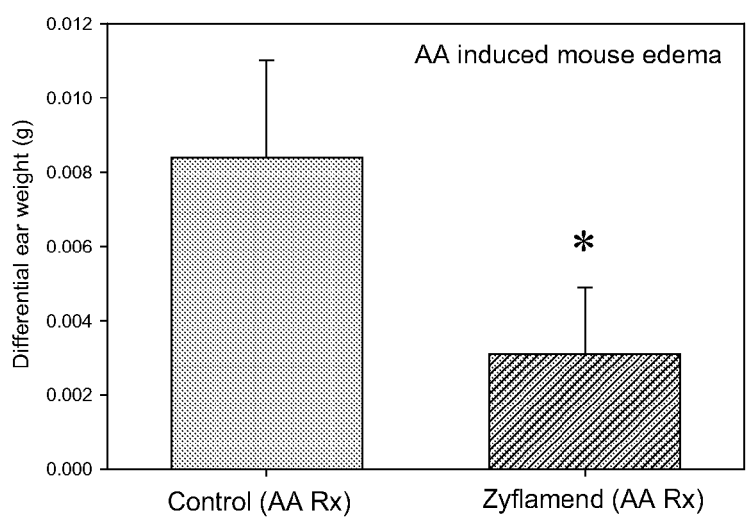
FIG. 6 is a graph depicting the anti-inflammatory effect of the inventive compounds on mouse ear edema.

FIG. 6 shows the anti-inflammatory effect of the inventive composition on mouse ear edema. The composition (10 ul) was administered topically to the right ear and only the acetonevehicle was applied to the left ear. One hour following AA treatment, the mouse was anesthetized and the ears "punched" to obtain a uniform piece of tissue. The weight of the right ear is then subtracted from that of the left ear to measure edema. The data reflect the relative ability of a given test substance to inhibit AA-mediated ear edema. Data are presented as mean+/−SD from 10 animals. * P<0.001 treatment versus AA (edema) control (AA mediated inflammation).

The data in FIG. 6 shows that the composition produces significant inhibition of arachidonic acid mediated inflammation.

Figure 10:
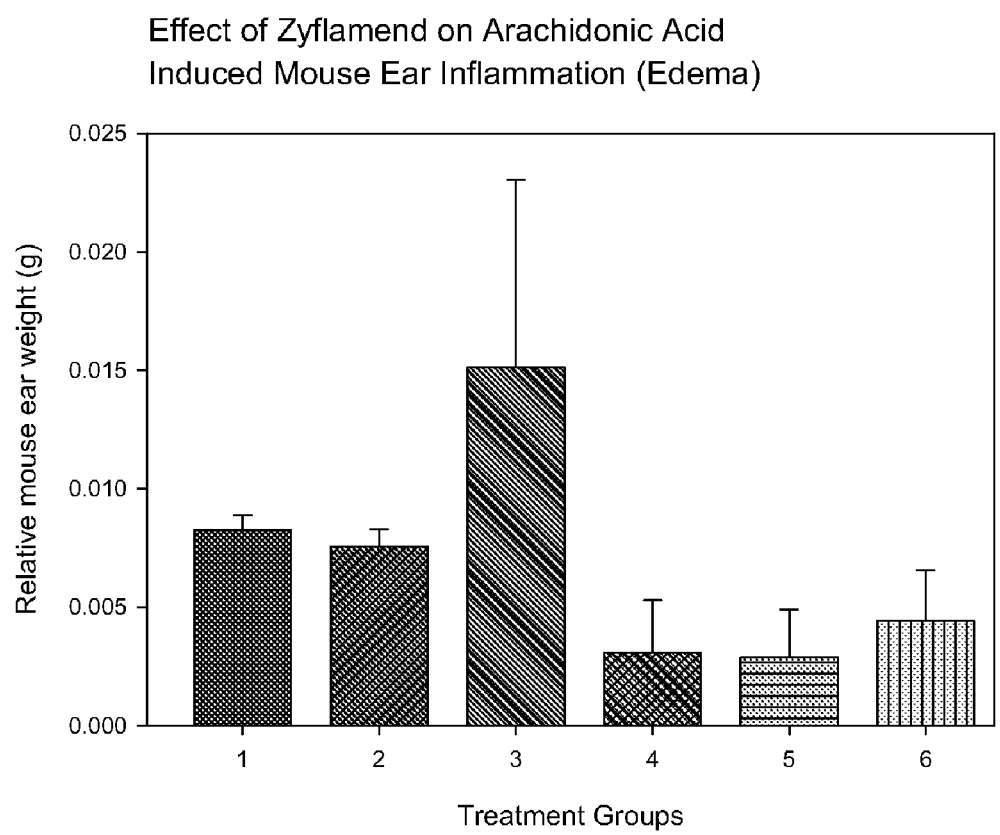
FIG. 10 is a graph depicting the effect of the inventive compositions on arachidonic acid (AA) mediated mouse ear edema.

Likewise, FIG. 10 shows the effect of the inventive composition on arachidonic acid mediated mouse ear edema. Treatment groups consisted of 1) olive oil control, 2) acetone control, 3) olive oil+AA, 4) The inventive composition (10 ul)+AA, 5) The inventive composition (5 ul)+AA, and 6) The inventive composition (2.5 ul)+AA. Data are provided as Mean±SD (n=10 mice/group). Once again, the composition inhibited the edema produced by AA. As shown in FIG. 10, a maximal inhibition of edema was obtained at all three composition "doses" although it appeared that the use of 2.5 ul of the composition may have been slightly less effective than either of the two higher concentrations.

Example 6

The Herbal Source and Relative Importance of 13-S-HODE in the Inventive Compositions In analyzing the relative eicosanoid content of the liquid form of the composition, it was surprising to see the large amount of 13-S-HODE. These analyses were done using LC/MS/MS in which an authentic deuterated standard was used to make sure we had the correct peak identity. To make doubly sure of this observation, the liquid composition was also analyzed using an enzyme linked immunoassay kit especially prepared for determination of 13-S-HODE. The results from the EIA analysis confirmed the mass spectrometry data and are shown in Table 3.

TABLE 3

Relative content of eicosanoids contained within the inventive composition

| Eicosanoid | PGE2 | 15-HETE | 12-HETE | 13-S-HODE |
|---|---|---|---|---|
| | 0.10* | 7.25 | 1.35 | 47.59 |

*Data are provided as ng eicosanoid/5 ul of oral composition

The fact that the oral form of the composition is 60% olive oil (which does not contain 13-S-HODE) indicates that the relative content of 13-S-HODE in extract material is even higher than is shown above.

Figure 7:
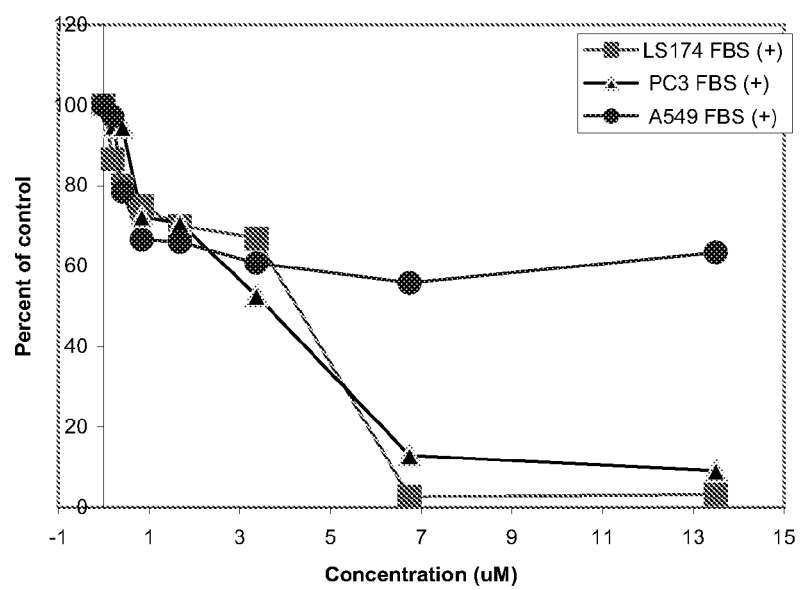
FIG. 7 is a graph depicting the effect of 13-S-HODE on proliferation of various cancer cell lines.

FIG. 7 shows the effect of 13-S-HODE on proliferation of various cancer cell lines. The data above indicate that 13-S-HODE, the product of the enzyme 15-LOX-2, can totally inhibit the growth of human tumor prostate (PC3) and colon (LS174) but not lung adenocarcinoma (A549) cell growth. The relative ability of 13-S-HODE to inhibit prostate and colon cancer cell lines with an $IC_{50}$ of about 3-4 uM. This is of importance when compared to the content of 13-S-HODE in the inventive composition. That is, as shown in Table 2 above there is sufficient 13-S-HODE within the composition to account for inhibition of cell growth. No doubt other factors within the composition also contribute to its ability to inhibit prostate and colon tumor cell growth but the ability of 13-S-HODE within the composition to be able to do this is of obvious interest.

The relative eicosanoid content of the liquid form of the composition was examined and it was surprising to see the large amount of 13-S-HODE. These analyses were done using LC/MS/MS in which an authentic deuterated standard was used to make sure the correct peak was identified. To make doubly sure of the observation, the liquid composition was also analyzed using an enzyme linked immunoassay kit especially prepared for determination of 13-S-HODE. The results from the EIA analysis confirmed the mass spectrometry data. The fact that the oral form of the composition is 60% olive oil (which does not contain 13-S-HODE) indicates that the relative content of 13-S-HODE in extract material is even higher than is shown above.

A search for the source of the eicosanoid product 13-S-HODE amongst the different herb and plant extract components that are used to make the composition was undertaken. The approach is to either solubilize the extract or subject the extract to a organic solvent mixture that will, in turn, pull out lipid soluble eicosanoids. These are then dried under nitrogen and reconstituted in a fixed volume of buffer compatible with the mass spectrometry equipment. Another aliquot is used for analyses of relative linoleic acid content using a GC/MS/MS. The rationale behind this is that 13-S-HODE can either be present as such in the extracts or it could also be derived through an enzymatic reaction in cells in culture if the cells contained 15-LOX-1 and were supplied with the substrate linoleic acid.

The data in Table 4 below show quite convincingly that, although there are extracts that contain both linoleic acid and 13-S-HODE, the eicosanoid is itself a component of several of the herbal extracts that are used to make the inventive composition. The fact that 13-S-HODE is absent from some extracts (e.g. green tea) is also interesting and lends credence to the fact that are measurements are correct.

TABLE 4

| Composition component | 13-HODE content (ng/mg extract) | Linoleic acid content (ug/mg extract) |
|---|---|---|
| Tumeric PSE | 32.55 | 0.78 |
| Rosemary SCE | 0.08 | 1.86 |
| Holy Basil | 1.42 | 1.15 |
| Green tea | 0.12 | None detected |
| Huzhang | 0.14 | 1.50 |
| Ginger SCE | 62.79 | 33.79 |
| Oregano SCE | 2.69 | 27.32 |
| Barberry | 10.41 | 0.27 |
| Rosemary | 0.36 | 1.46 |
| Tumeric SCE | 16.30 | 31.10 |
| Chinese Goldenthread | 13.46 | 0.81 |
| *Scutellaria* | 0.64 | None detected |
| Ginger PSE | 17.20 | 0.37 |

Both the determinations of 13-HODE as well as linoleic acid have been performed three times with comparable results. The 13-S-HODE was determined using LC/MS/MS while linoleic acid content was measured using a GC/MS/MS. The sources of the composition's 13-S-HODE appear to be mostly due to ginger and tumeric. It is interesting that this particular eicosanoid is present in both the PSE and the SCE extracts of ginger and to a lesser extent in tumeric root as well. Notably, the presence of high amounts of 13-HODE is not always associated with high amounts of linoleic acid, the substrate for 15-LOX-1 which produces 13-S-HODE.

Example 7

Osteoclast Differentiation Assay

To determine the effect of the inventive compositions on receptor activator of NF-κB ligand (RANKL)-induced osteoclastogenesis, Applicants cultured RAW 264.7 cells, which can differentiate into osteoclasts by RANKL in vitro. RAW 264.7 cells were cultured in 24-well dishes at a density of 1 ×10$^4$ cells per well and allowed to adhere overnight. The medium was then replaced, and the cells were coincubated with different concentrations of the inventive compositions and 5 nM RANKL. At days 5, the cells were stained for tartrate-resistant acid phosphatase (TRAP) expression, as previously described using an acid phosphatase kit (Sigma-Aldrich), and the TRAP-positive multinucleated osteoclasts (>3 nuclei) per well were counted.

Figure 11A:
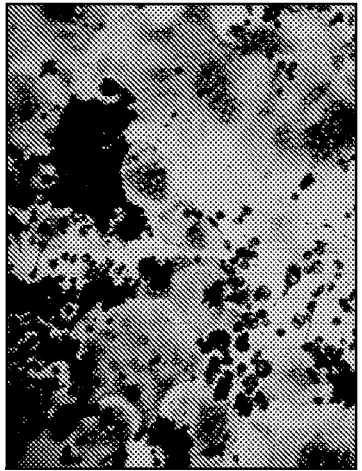
FIG. 11(A) is a series of photographs depicting TRAP-positive RAW 264.7 cells following incubation either alone or in the presence of 5 nM RANKL with 0.8 mg/ml of the inventive composition for 5 days.
Figure 11A:
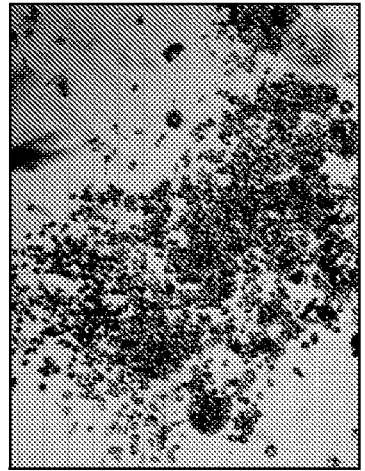
Figure 11A:
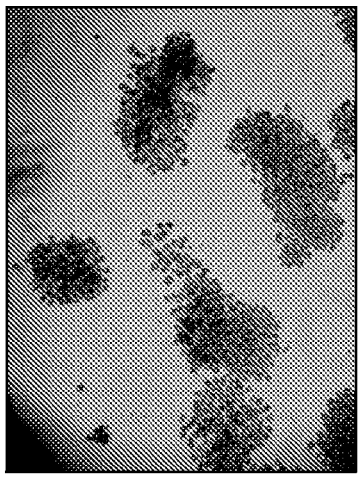
Figure 11A:
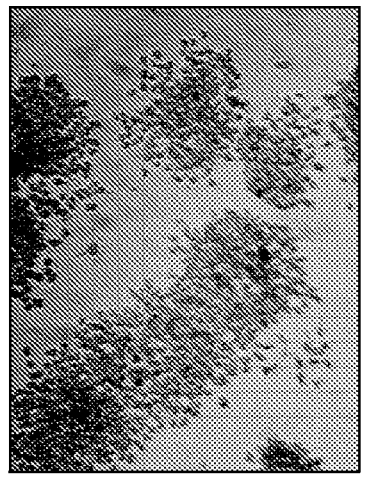

RAW 264.7 cells (1×10$^4$ cells/well) were incubated either alone or in the presence of 5 nM RANKL with 0.8 mg/ml the inventive compositions for 5 days and stained for TRAP expression. As shown in FIG. 11(A), TRAP-positive cells were photographed (original magnification, 100×).

RAW 264.7 cells (1×10$^4$ cells/well) were incubated either alone or in the presence of 5 nM RANKL with The inventive compositions at the indicated concentrations for 5 days and stained for TRAP expression. Multinucleated (three nuclei) osteoclasts were counted, with the results depicted graphically in FIG. 11(B).

Figure 11B:
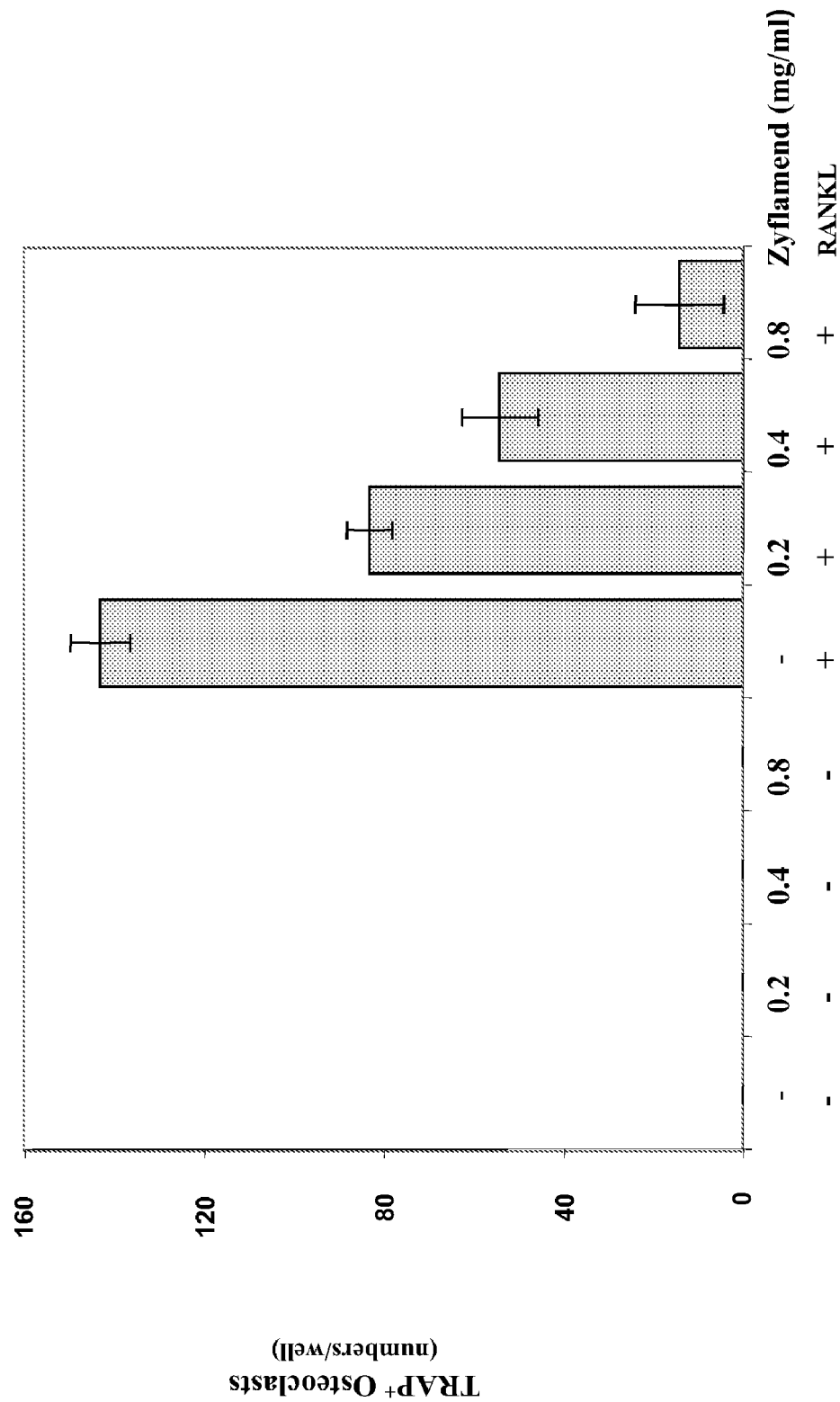
FIG. 11(B) is a graph depicting the number of multinucleated (three nuclei) osteoclasts counted in RAW 264.7 cells following incubation either alone or in the presence of 5 nM RANKL with 0.8 mg/ml of the inventive compositions for 5 days.

It is shown that the inventive compositions suppress RANKL-induced osteoclastogenesis. Because RANKL, a member of the TNF superfamily, induces osteoclastogenesis through the activation of NF-κB, Applicants determined whether the inventive compositions can suppress RANKL-induced osteoclastogenesis. Applicants found that RANKL induced osteoclast differentiation, as indicated by the expression of TRAP, as shown in FIG. 11(A), and that the inventive compositions suppressed it in a dose-dependent manner, as shown in FIG. 11(B).

Example 8

Invasion Assay

The membrane invasion culture system was used to assess cell invasion because invasion through the extracellular matrix is a crucial step in tumor metastasis. The BD BioCoat Tumor Invasion system is a chamber that has a light-tight polyethelyene terephthalate membrane with 8 μm-diameter pores and is coated with a reconstituted basement membrane gel (BD Biosciences, San Diego, Calif.). A total of H1299 (2.5×10$^4$ cells) were suspended in serum-free medium and seeded into the upper wells. After incubation overnight, cells were coincubated with different concentrations of the inventive compositions and 1 nM TNF for a further 24 h in the presence of 1% FBS. The cells that invaded through the Matrigel (i.e., those that migrated to the lower chamber during incubation) were stained with 4 μg/ml Calcein AM (Molecular Probes, Eugene, Oreg.) in PBS for 30 min at 37° C. and scanned for fluorescence with a Victor3 multi-plate reader (Perkin Elmer Life and Analytical Sciences, Boston, Mass.); fluorescent cells were counted.

Figure 12:
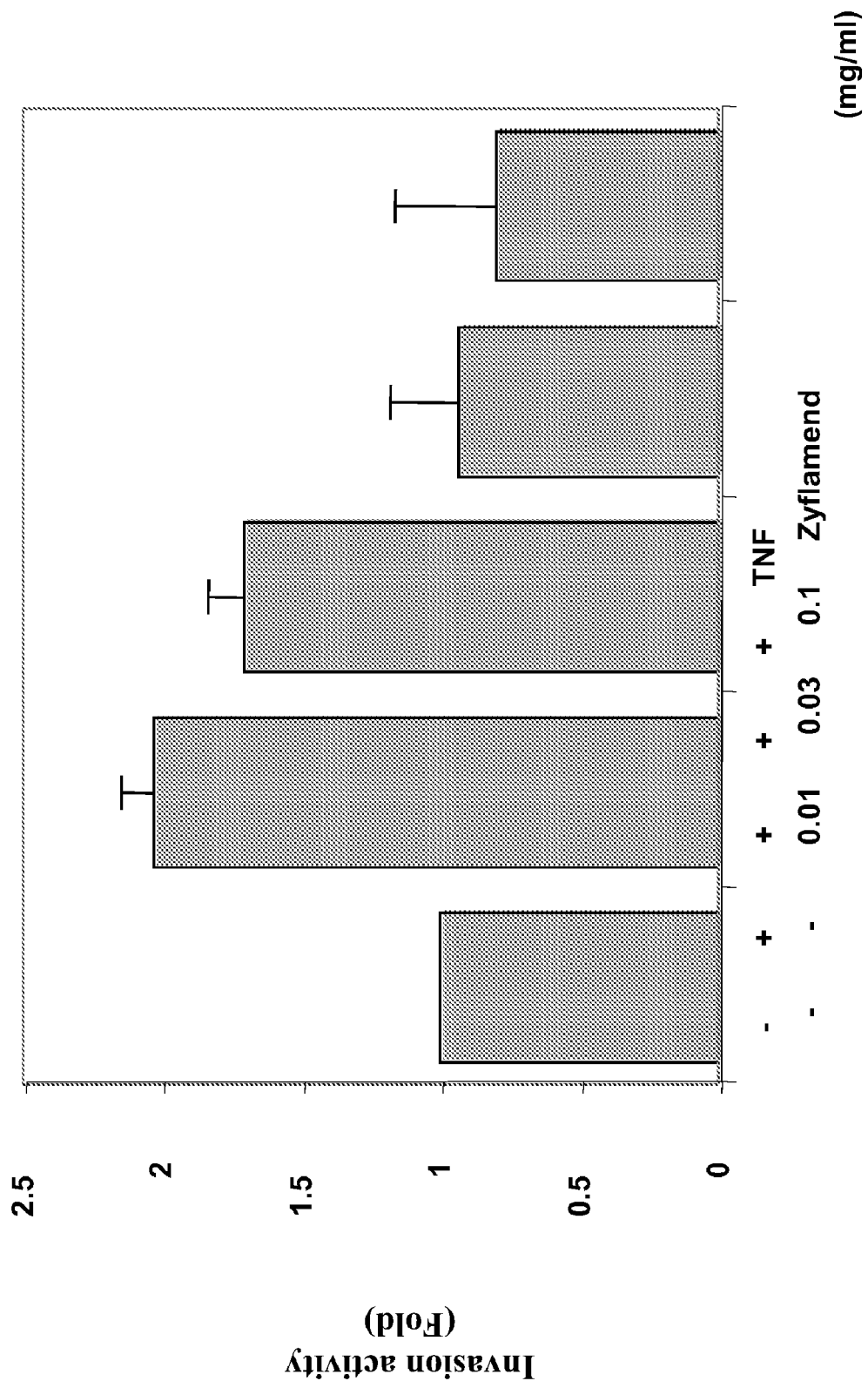
FIG. 12 is a graph depicting an invasion assay of a Matrigel invasion chamber after overnight coincubation of 0.3 mg/ml of the inventive compositions and 1 nM TNF for 24 h in the presence and in the absence of 1% serum.

H1299 cells (2.5×10$^4$ cells/well) were seeded into the upper wells of a Matrigel invasion chamber overnight in the absence of serum, coincubated with 0.3 mg/ml the inventive compositions and 1 nM TNF for 24 h in the presence of 1% serum, and then subjected to invasion assay, with the results depicted graphically as shown in FIG. 12. The value for none of the inventive compositions and no TNF was set to 1.0.

It is shown that the inventive compositions suppresses TNF-induced tumor cell invasion activity. It is known that NF-κB regulates the expression of gene products (e.g., MMP-9, COX-2, and VEGF) that mediate tumor cell invasion. Whether the inventive compositions can modulate TNF-induced tumor cell invasion activity, was investigated in vitro. To determine this, tumor cells were seeded to the top chamber of the matrigel invasion chamber with TNF in the presence or absence of the inventive compositions, and then examined for invasion. As shown in FIG. 12, TNF-induced tumor cell invasion by almost 2 fold and the inventive compositions suppressed this activity in a dose-dependent manner. The inventive compositions alone had no effect on invasion activity.

Example 9

LIVE/DEAD Assay

To measure apoptosis, Applicants used the LIVE/DEAD assay (Molecular Probes, Eugene, Oreg.), which determines intracellular esterase activity and plasma membrane integrity. This assay employs calcein, a polyanionic dye, which is retained within the live cells and provides green fluorescence. It also employs the ethidium monomer dye (red fluorescence), which can enter the cells only through damaged membranes and bind to nucleic acids but is excluded by the intact plasma membrane of live cells. Briefly, 1×10$^6$ cells were incubated with 0.5 mg/ml of the inventive compositions for 24 h and then treated with 1 nM TNF or various chemotherapeutic agents for 16 h at 37° C. Cells were stained with the LIVE/DEAD reagent (5 μM ethidium homodimer, 5 μM calcein-AM) and then incubated at 37° C. for 30 min. Cells were analyzed under a fluorescence microscope (Labophot 2; Nikon, Tokyo, Japan).

Figure 13:
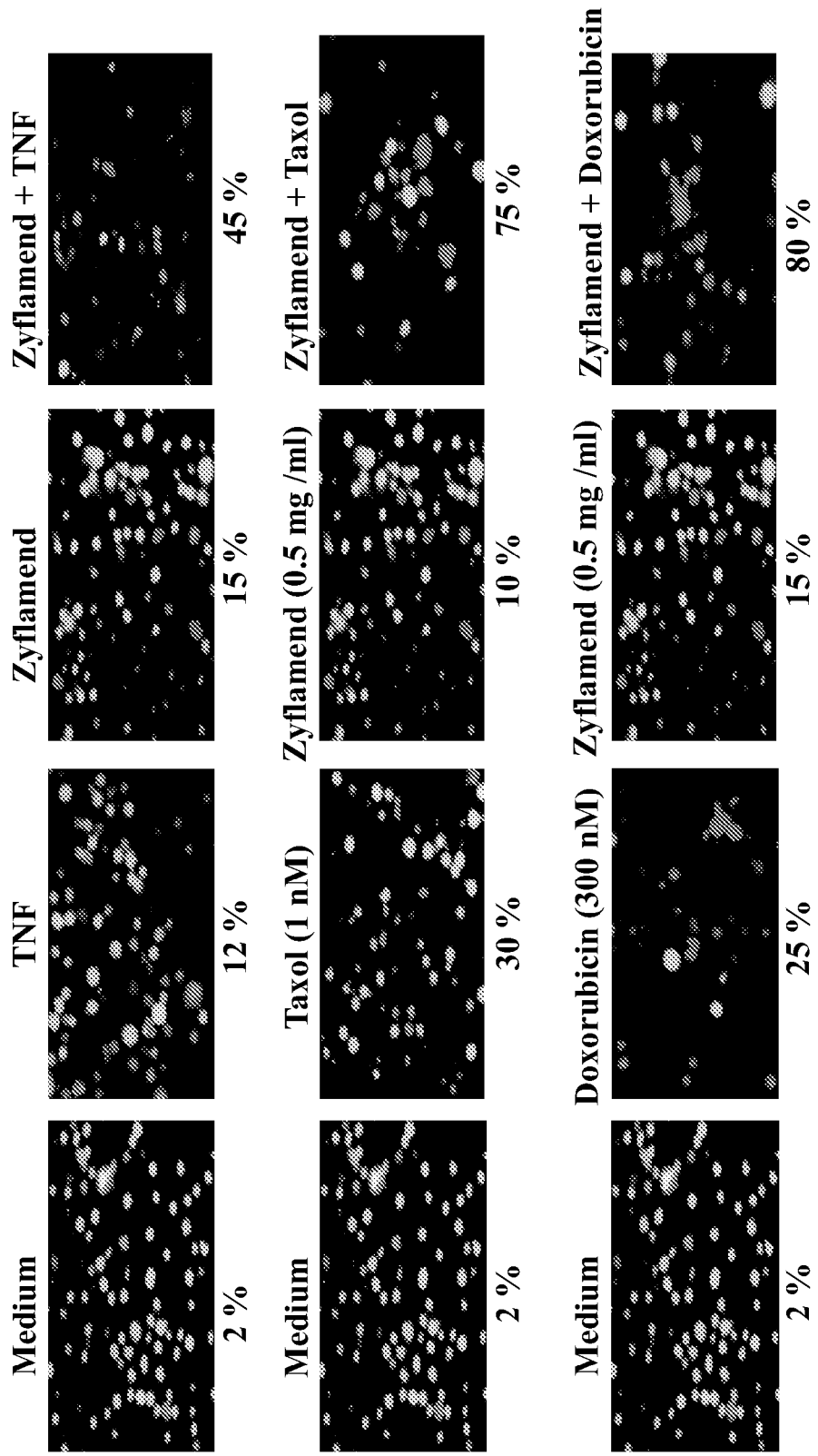
FIG. 13 is a series of photographs depicting cell death of human multiple myeloma U266 cells incubated with 1 nM TNF, 1 nM taxol, and 300 nM doxorubicin, alone or in combination with 0.5 mg/ml of the inventive compositions, determined by calcein AM based LIVE/DEAD assay as described herein. Red color highlights dead cells, and green color highlights live cells.

Human multiple myeloma U266 cells (1×10$^6$ cells/ml) were serum starved for 24 h and then incubated with 1 nM TNF, 1 nM taxol and 300 nM doxorubicin alone or in combination with (0.5 mg/ml) of the inventive compositions as indicated for 24 h. Cell death was determined by calcein AM based LIVE/DEAD assay, as shown in FIG. 13. Red color highlights dead cells, and green color highlights live cells.

The inventive compositions potentiate the apoptotic effects of TNF and chemotherapeutic drugs. Because NF-κB activation has been shown to inhibit the apoptosis induced by various agents, whether the inventive compositions will modulate the apoptosis induced by TNF and chemotherapeutic agents, was investigated. The effect of the inventive compositions on TNF and chemotherapeutic agent-induced apoptosis was examined by the LIVE/DEAD assay. The LIVE/DEAD assay, which measures intracellular esterase activity and plasma membrane integrity, indicated that the inventive compositions enhances the apoptotic effects of TNF, taxol, and doxorubicin against tumor cells.

Example 10

Electrophoretic Mobility Shift Assays of NF-κB Activation

To determine NF-κB activation, Applicants carried out electrophoretic mobility shift assays (EMSA) essentially as previously described in Chaturvedi, M. M., Mukhopadhyay, A. and Aggarwal, B. B. (2000) Assay for redox-sensitive transcription factor. *Methods Enzymol.*, 319, 585-602. Briefly, nuclear extracts ($1 \times 10^6$ cells/ml) were incubated with $^{32}$P-end-labeled 45-mer double-stranded NF-κB oligonucleotide (15 µg of protein with 16 fmol of DNA) from the human immunodeficiency virus long terminal repeat, 5'-TTGTTA-CAA GGGACTTTC CGCTG GGGACTTTC CAGGGAG-GCGTGG-3' (boldface indicates NF-κB-binding sites), for 30 min at 37° C., and the DNA-protein complex formed was separated from free oligonucleotide on 6.6% native polyacrylamide gels. A double stranded mutated oligonucleotide, 5'-TTGTTACAA CTCACTTTC CGCTG CTCACTTTC CAGGGAGGCGTGG-3', was used to examine the specificity of binding of NF-κB to the DNA. The dried gels were visualized, and the radioactive bands were quantitated using a Storm 820 phosphorimager with the ImageQuant software program (Amersham, Piscataway, N.J.).

Figure 14A:
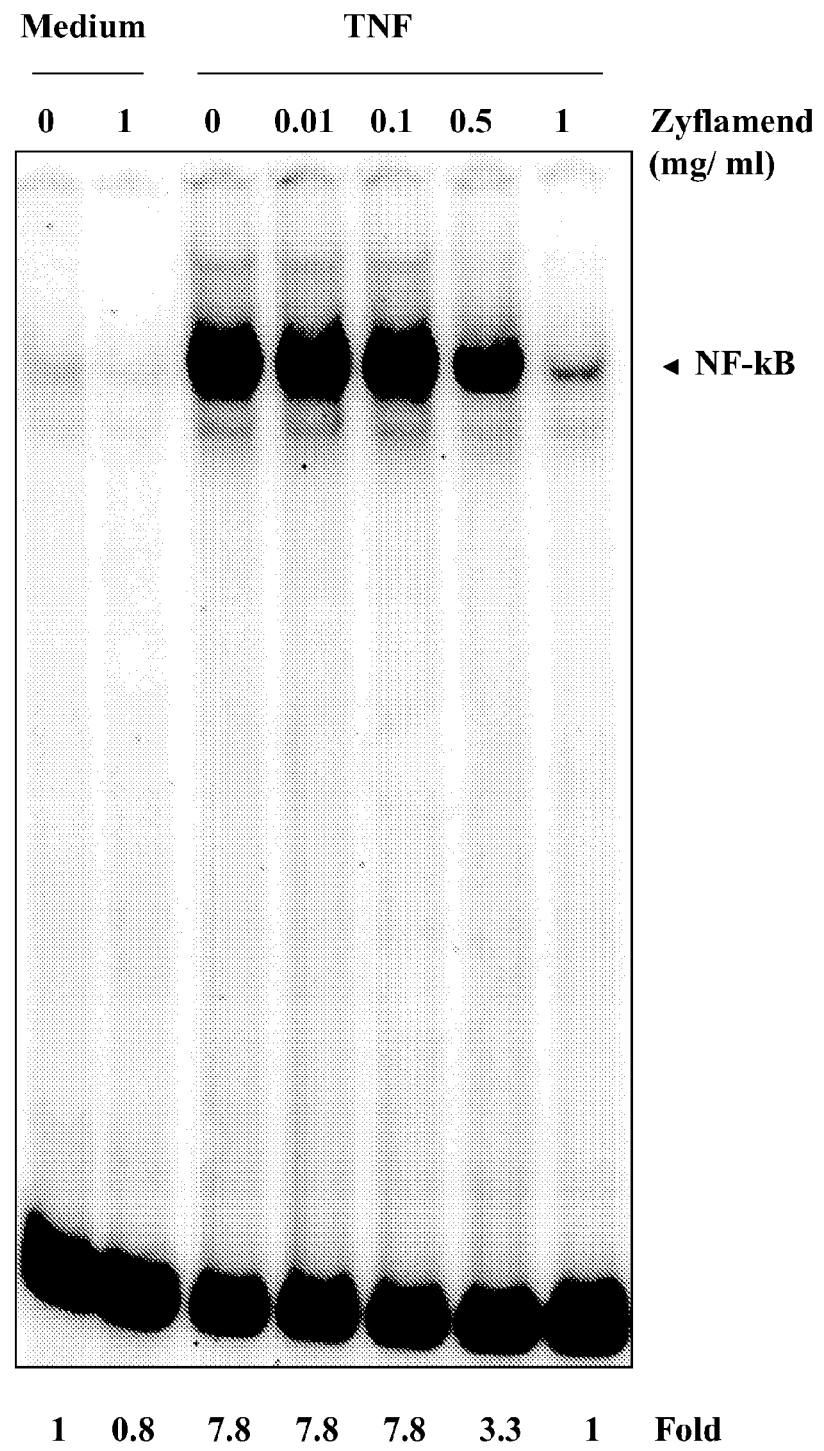
FIG. 14(A) is a photograph depicting NF-κB activation of KBM-5 cells preincubated with indicated concentrations of the inventive compositions and treated with 0.1 nM TNF for 30 min.

KBM-5 cells ($2 \times 10^6$ cells/ml) were preincubated with indicated concentrations of the inventive compositions for 1 h, treated with 0.1 nM TNF for 30 min. The nuclear extracts were assayed for NF-κB activation by EMSA, as shown in FIG. 14(A).

The inventive compositions suppress NF-κB activation in a dose- and time-dependent manner. As NF-κB plays an important role in apoptosis and in cell invasion, Applicants examined the effect of the inventive compositions on activation of this transcription factor. Applicants first investigated the effect of the inventive compositions on the activation of NF-κB induced by TNF in human myelogenous leukemia (KBM-5) cells. DNA-binding assay (EMSA) results showed that the inventive compositions alone had no effect on NF-κB activation. However, it inhibits TNF-mediated NF-κB activation in a dose-dependent manner, as shown in FIG. 14(A).

Figure 14B:
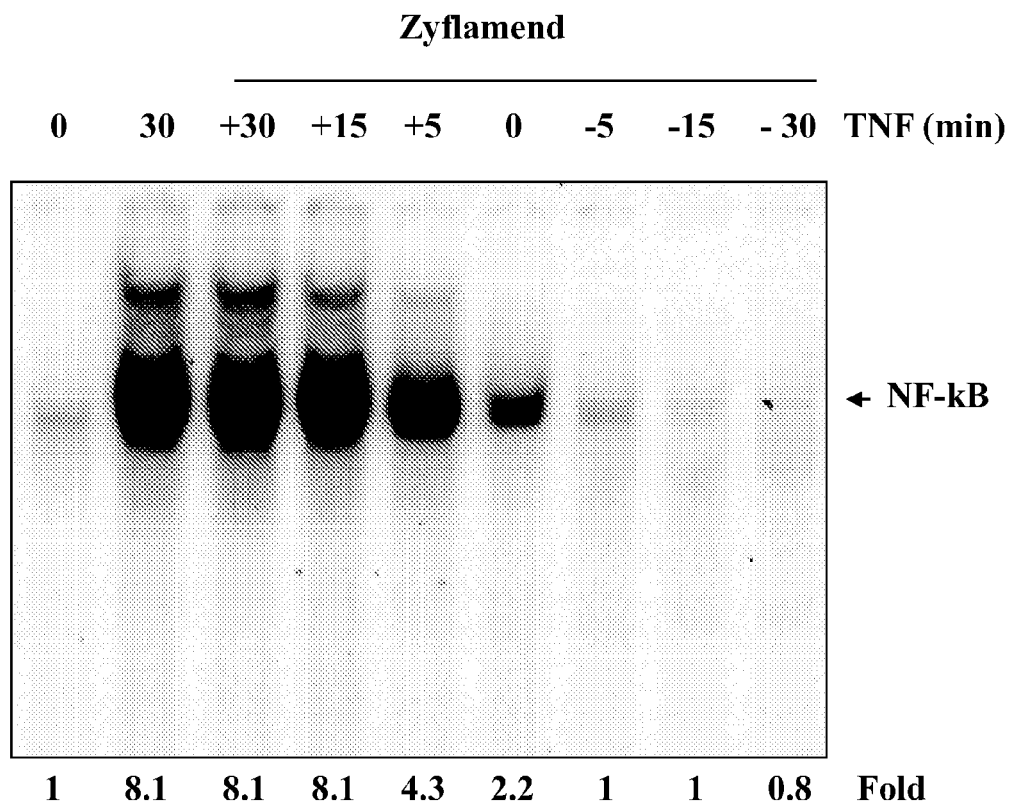
FIG. 14(B) is a photograph depicting NF-κB activation of KBM-5 cells preincubated with 1 mg/ml of the inventive compositions and treated with 0.1 nM TNF for 30 min.

KBM-5 cells ($2 \times 10^6$ cells/ml) were preincubated with 1 mg/ml of the inventive compositions for the indicated times and then treated with 0.1 nM TNF for 30 min. The nuclear extracts were assayed for NF-κB activation by EMSA, as shown in FIG. 14(B). The suppression of NF-κB activation by The inventive compositions were also found to be time-dependent.

Figure 14C:
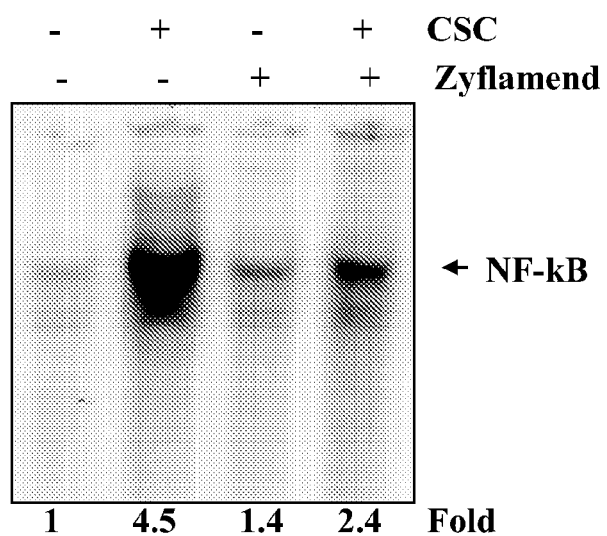
FIG. 14(C) is a photograph depicting NF-κB activation of KBM-5 cells preincubated with 1 mg/ml of the inventive compositions and treated with cigarette smoke (10 μg/ml) for 1 h.

The inventive compositions inhibit cigarette smoke-induced NF-κB activation. H1299 cells were preincubated with the inventive compositions (1 mg/ml) for 1 h, then treated with cigarette smoke (10 µg/ml) for 1 h. The nuclear extracts were assayed for NF-κB activation by EMSA, as shown in FIG. 14(C).

The inventive compositions block NF-κB activation induced by cigarette smoke condensate. Applicants next examined the effect of the inventive compositions on the activation of NF-κB induced by cigarette smoke condensate in non-small lung adenocarcinoma H1299 cells. DNA-binding assay (EMSA) results showed that the inventive compositions suppressed the NF-κB activation induced by cigarette smoke condensate, as shown in FIG. 14(C). These results suggest that the inventive compositions acted at a step in the NF-κB activation pathway that is common to TNF and cigarette smoke condensate.

Example 11

Western Blot Analysis of TNF-induced Gene Expression

To determine the effect of the inventive compositions on TNF-induced expression of COX-2, VEGF, ICAM-1, MMP-9, cIAP-1/2, survivin, Bfl-1/A1, Bcl-2, Bclx$_L$, cFLIP, TRAF1, and XIAP in whole-cell extracts of treated cells ($2 \times 10^6$ cells/ml), 30 µg of protein was resolved on SDS-PAGE and probed by Western blot with specific antibodies as per manufacturer's recommended protocol. The blots were washed, exposed to HRP-conjugated secondary antibodies for 1 h, and finally detected by ECL reagent (Amersham Pharmacia Biotechnology, Piscataway, N.J.).

Figure 15A:
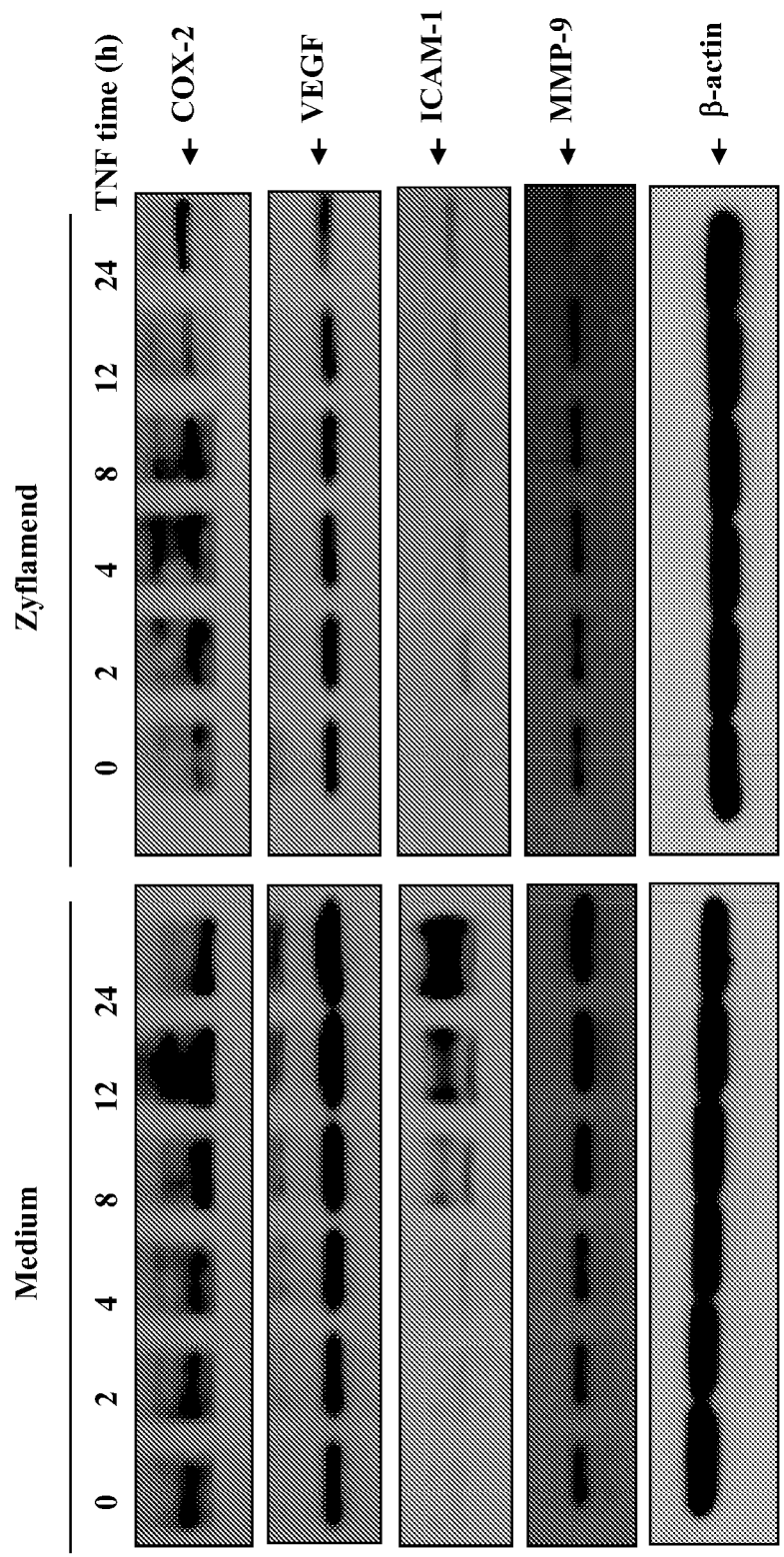
FIG. 15(A) is a photograph depicting the expression of proliferative and metastatic proteins in KBM-5 cells incubated with 1 mg/ml of the inventive compositions for 1 h and treated with 1 nM TNF for the indicated times.

The inventive compositions inhibit TNF-induced NF-κB dependent gene products involved in the proliferation and metastasis of tumor cells. Applicants also investigated whether the inventive compositions can modulate NF-κB dependent gene products involved in the proliferation and metastasis of tumor cells. TNF has been shown to induce COX-2, MMP-9, ICAM-1, and VEGF, all of which have NF-κB binding sites in their promoters. As shown in FIG. 15(A), TNF treatment induced the expression of COX-2, VEGF, ICAM-1, and MMP-9 gene products and the inventive compositions abolished the expression.

Figure 15B:
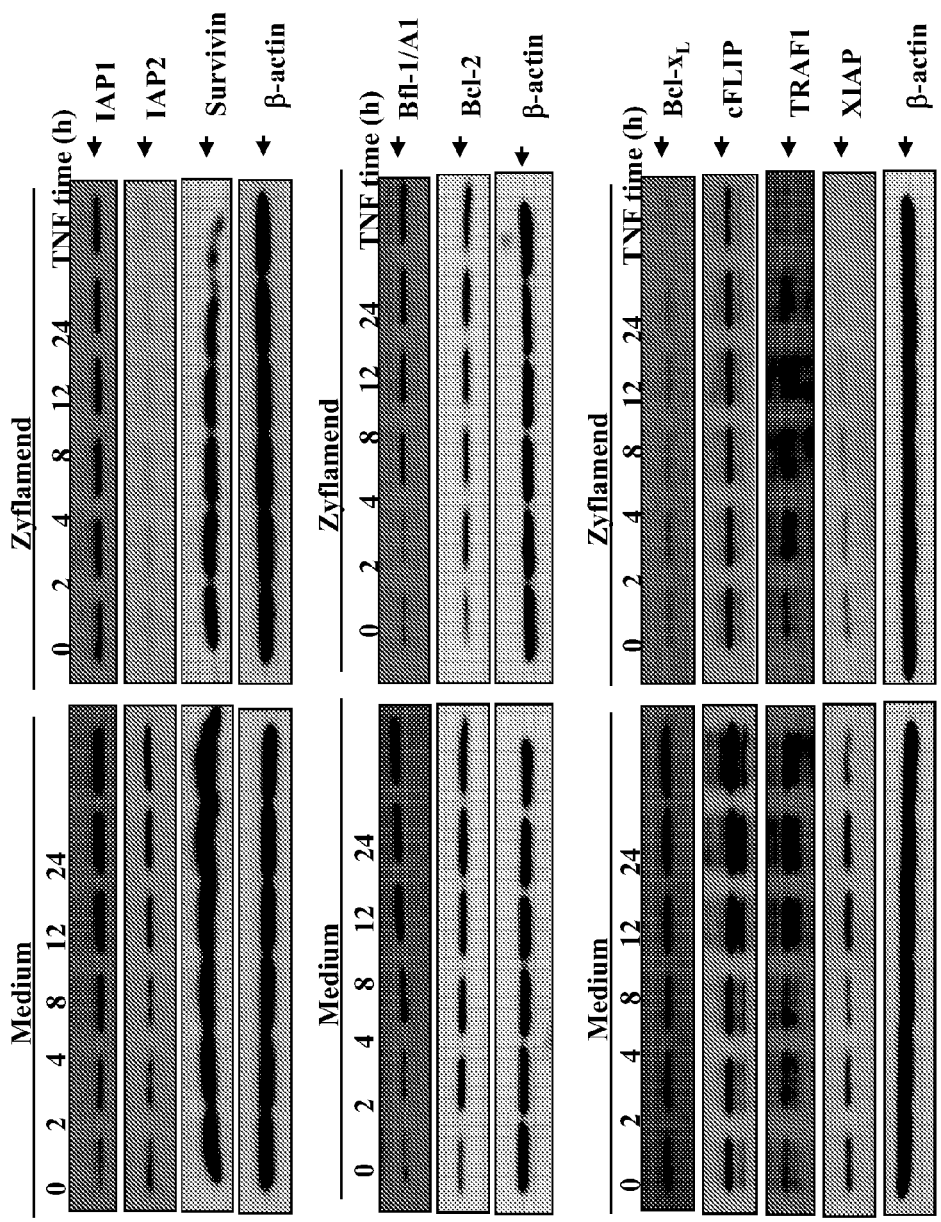
FIG. 15(B) is a photograph depicting the expression of anti-apoptotic proteins in KBM-5 cells incubated with 1 mg/ml of the inventive compositions for 1 h and treated with 1 nM TNF for the indicated times.

KBM-5 cells ($2 \times 10^6$ cells/ml) were incubated with 1 mg/ml of the inventive compositions for 1 h and then treated with 1 nM TNF for the indicated times. Whole-cell extracts were prepared and subjected to Western blot analysis using the indicated antibodies, as shown in FIG. 15(B).

The inventive compositions inhibit TNF-induced NF-κB dependent anti-apoptotic gene products. NF-κB upregulates the expression of the antiapoptotic proteins IAP1, IAP2, survivin, Bfl-1/A1, Bcl-2, Bcl-XL, cFLIP, TRAF1, and XIAP. Applicants next investigated whether the inventive compositions affects the expression of these gene products. Applicants found that the inventive compositions inhibits the TNF-induced as well as the basal expression of all of these proteins, as shown in FIG. 15(B).

Example 12

Evidence of $G_2$/M Arrest of PC3 Cells Mediated by the Inventive Compositions

As shown in FIGS. 16(A)-(D), treatment of PC3 cells with the inventive compositions produces concentration-dependent inhibition of the cell cycle. The herbal product produces a clear $G_2$/M accumulation of cells that is evident even at concentrations as low as 0.28 ul/ml. At higher concentrations, the $G_2$/M phase is more evident as is a sub $G_o$ peak indicative of apoptosis. Concomitant with the rise in numbers of cells in G₂/M there is a progressive concentration-dependent fall of cells in the G1 portion of the cell cycle. Only 10% of control cells are routinely present at the G₂/M phase, while treatment with 0.57 ul/ml of the inventive compositions results in greater than 40% of cells in a G₂/M block.

Figure 16A:
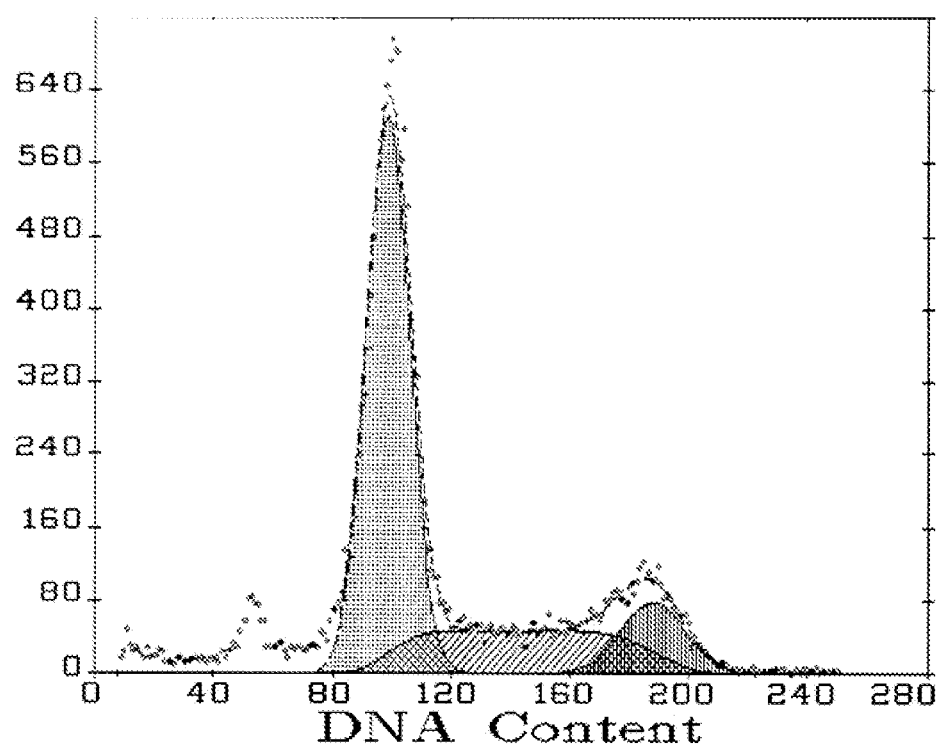
FIGS. 16(A)-(D) are a series of graphs depicting cell cycle distribution plots.
Figure 16B:
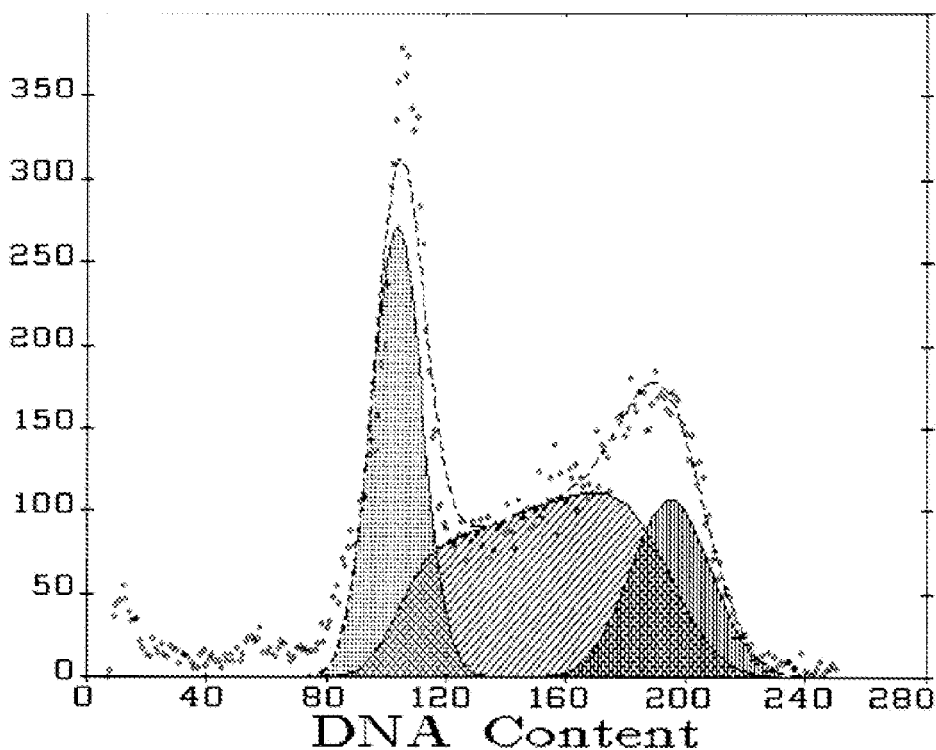
Figure 16C:
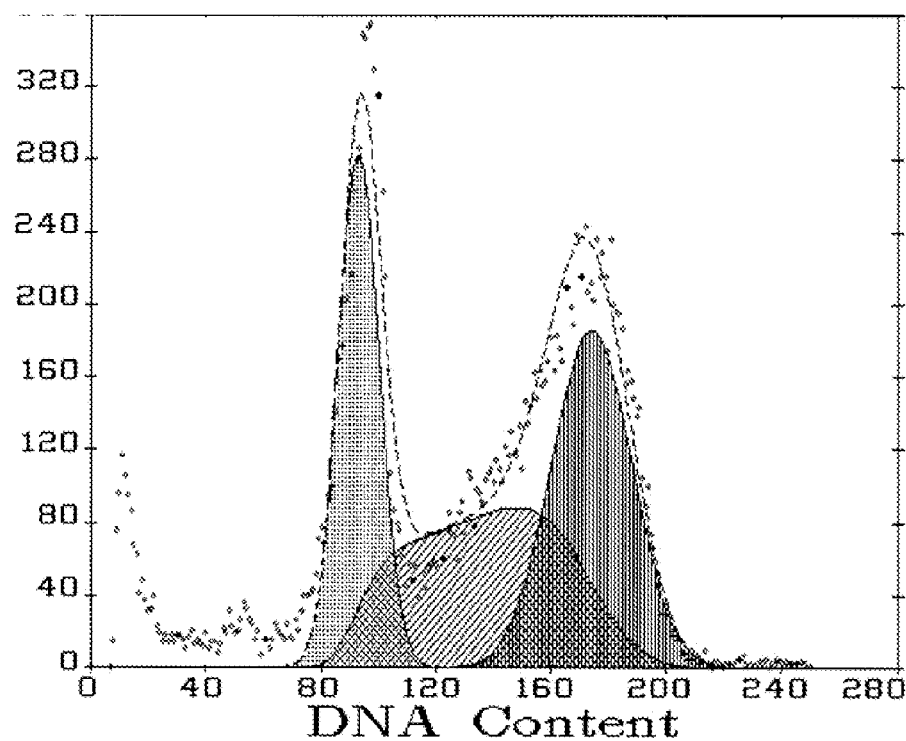
Figure 16D:
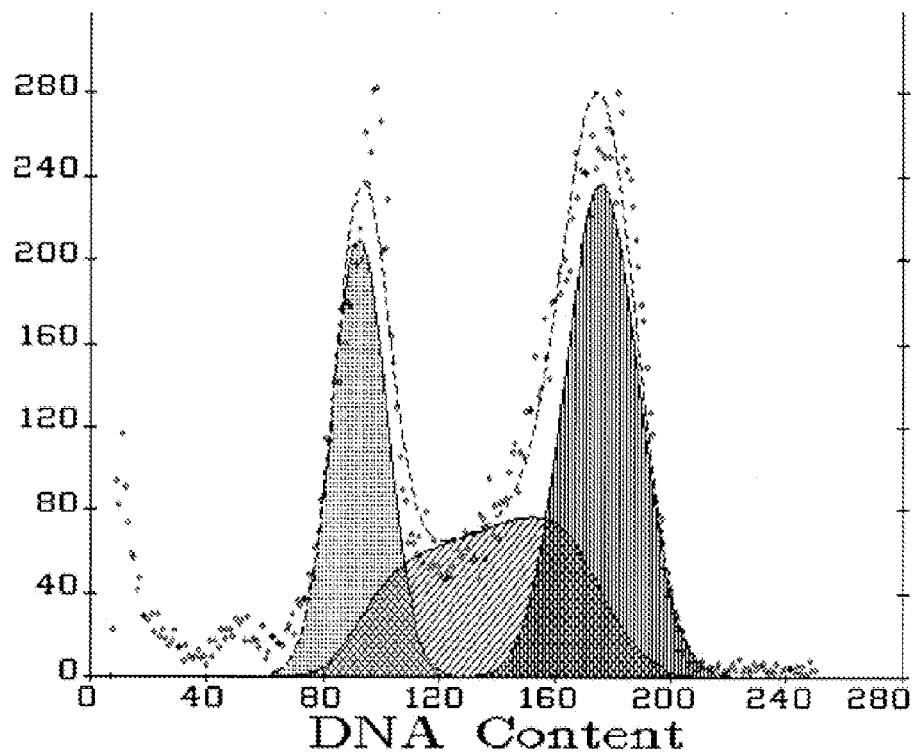
Figure 17A:
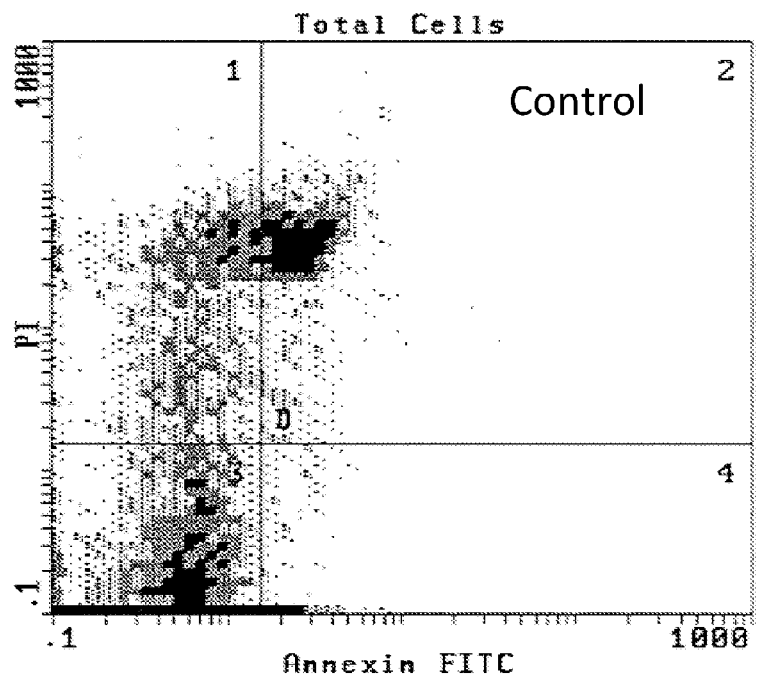
FIGS. 17(A)-(D) are a series of graphs depicting PC3 cells treated with the inventive compositions at indicated concentrations (FIG. 17(A)=0% control.
Figure 17B:
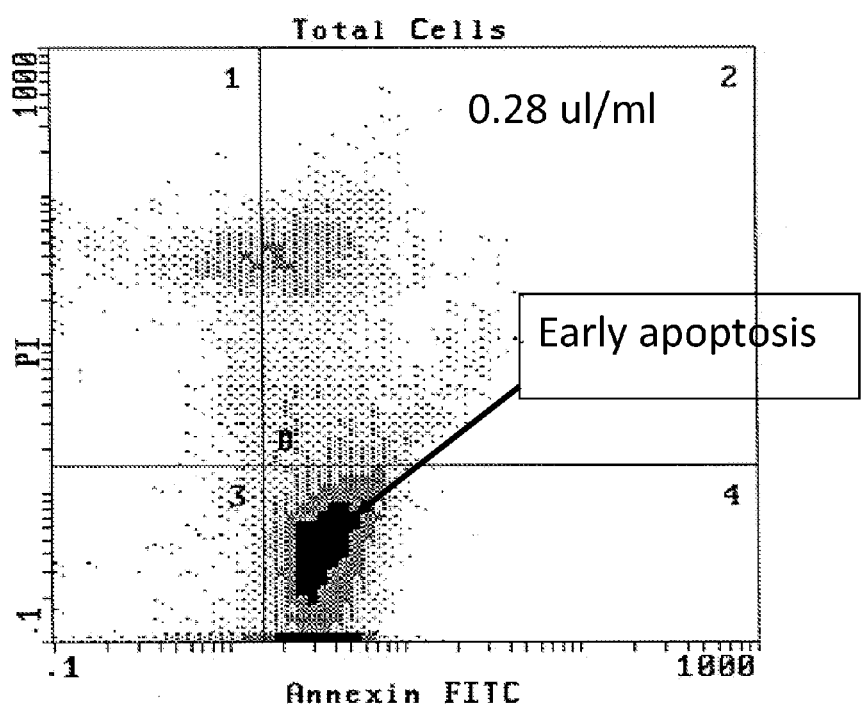
Figure 17C:
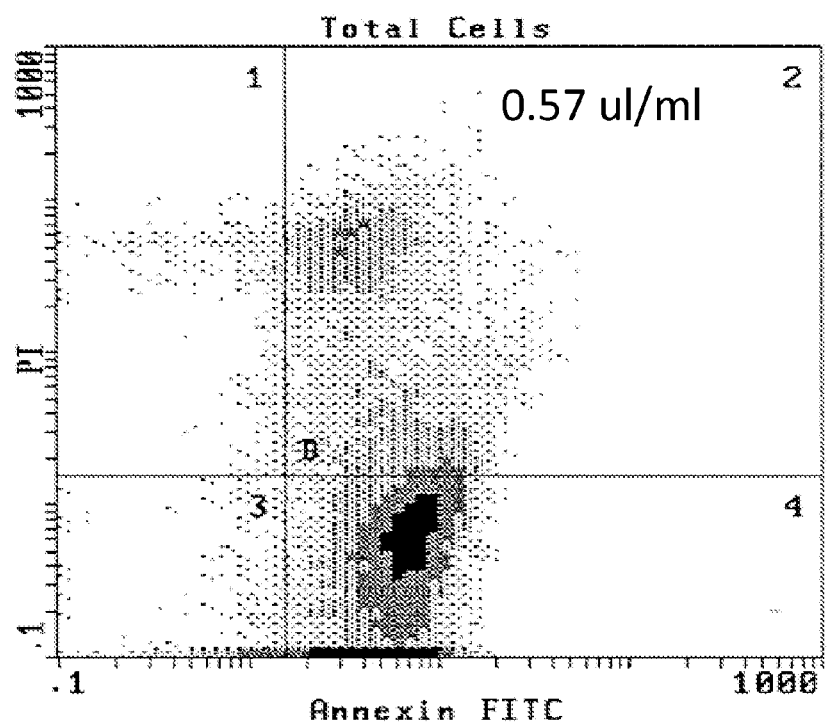
Figure 17D:
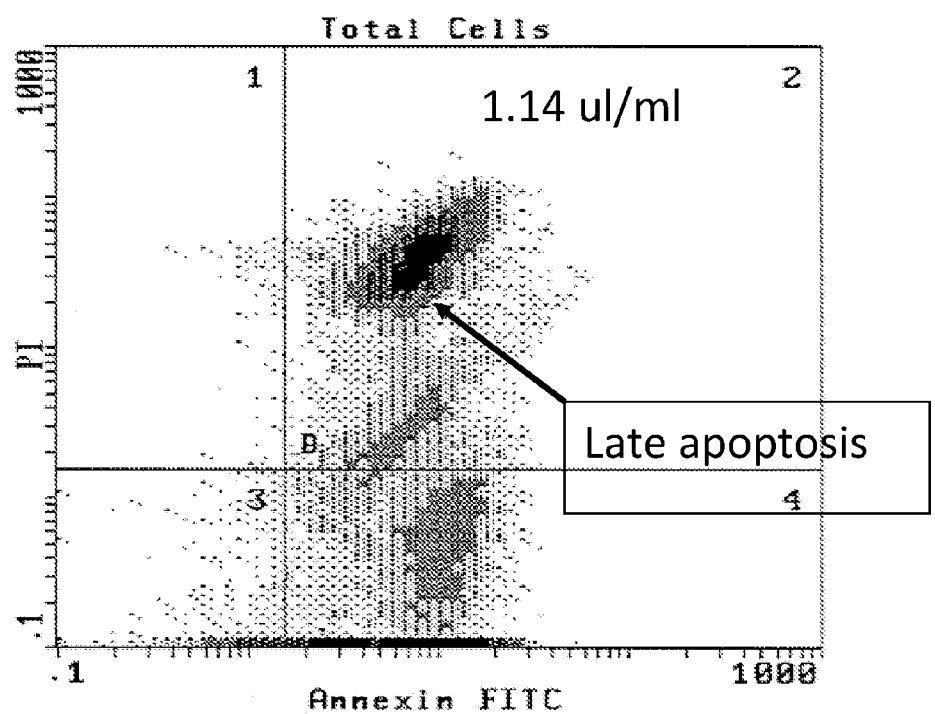

As shown in FIG. 16(A), the upper left plot demonstrates a normal cell cycle distribution of PC3 cells. The G2/M percentage of cells is small (small dark shaded peak to the right in the figure. In FIG. 16(B) PC3 cells have been treated with 0.28 ul of the inventive compositions/ml tissue culture media. The size of the G2/M peak increases. FIG. 16(C) (0.57 ul of the inventive compositions/ml) and FIG. 16(D) (1.14 ul/ml) show an increasing cell cycle block due to increased concentration of the inventive compositions.

Comparing FIGS. 16(A)-(D) a clear concentration dependent increase in the percentage of cells in the G2/M phases of the cell cycle is observed while this is an associated decrease in the cells in the G1 phase of the cell cycle.

Example 13

Flow Cytometry Analyses of Apoptosis Mediated by the Inventive Compositions

As shown in FIGS. 17(A)-(D), concentrations of the inventive compositions that produced only low levels of G₂/M block were found to be associated with induction of early apoptosis as evidenced by staining of cells with annexin V and phosphatidylinositol (PI). Even at the lowest concentration examined, 0.28 ul/ml (FIG. 17(B)), clear evidence of annexin V binding to inverted membrane phosphatidylserine is evident by flow cytometry of the inventive compositions treated PC3 cells. Further evidence of the multiherb mediated production of apoptosis is in the concentration response of propidium iodide binding to nucleic acids in later stages of cell death following the breach of membrane integrity.

As shown in FIGS. 17(A)-(D), PC3 cells were treated with the inventive compositions at indicated concentrations for 24 hr. Cells were then stained with Annexin V and PI solution. Apoptosis was measured by flow cytometry analyses (FACS). Even at a low concentration of 0.28 ul/ml there is a clear indication of early apoptosis. At concentrations in excess of 1.1 ul/ml most cells have died and appear in a late apoptosis (cell death) stage.

Comparing FIGS. 17(A)-(D) a clear concentration-dependent increase in PI staining is observed which is indicative of cell membrane alteration, a hallmark of early apoptosis. Annexin V staining even at the lowest concentration of the inventive compositions indicates DNA staining associated with apoptosis. The percentage of cells stained with Annexin V declines with increasing concentration of the inventive compositions due to cell death.

Example 14

Changes in Eicosanoid Metabolism Mediated by the Inventive Compositions

As shown in FIGS. 18(A)-(D), treatment of cloned human COX-1, COX-2 and 5-LOX enzymes produces a concentration dependent inhibition of formation of respective eicosanoid products, PGE₂ and 5-HETE, with formation of 5-LOX more potently inhibited than either COX-1 or COX-2 (data not shown). Cellular changes in eicosanoid metabolism due to incubation with the inventive compositions were then examined. As seen in FIGS. 18(A)-(D), treatment of PC3 cells with the inventive compositions produced a decrease in formation of PGE₂ (FIG. 18(A)) and 5-HETE (FIG. 18(B)). More impressive, however, was the cellular decline in 12-HETE levels presumably resulting from inhibition of 12-LOX activity. Concentrations of the inventive compositions as low as 0.25 ul/min produced a significant reduction in 12-HETE levels compared to untreated control cells. The highest concentration of the inventive compositions examined (1 ul/ml) resulted in an approximate 80% reduction in 12-HETE levels within PC3 cells (FIG. 18(C)).

The treatment of PC3 cells with the inventive compositions also produced a clear decrease in cellular content of 5-LOX protein as evidenced by Western blot analysis (FIG. 18(D)). A decline in 12-LOX protein content was also evident at concentrations of the inventive compositions higher than 0.25 ul/ml. The increase in COX-2 protein due to incubation of PC3 cells with higher levels of the inventive compositions is reminiscent of elevations of this enzyme due to treatment of cells with other anti-inflammatory agents such as celecoxib.

The data in Table 5 were derived from phosphoprotein analyses of PC3 cell lysates after treatment with nontoxic concentrations of either the inventive compositions or baicalein, a component of *Scutellaria*. Proteins were separated using gel electrophoresis and then the gel was probed with monoclonal antibodies to the proteins. The antibodies could detect differences in phosphorylation status of the proteins. Gels were then quantified using a densitometer. Only relative changes (although significant) are indicated in the table above. There are many similarities in the changes in phosphorylation status signaling similar up regulation or down regulation of proteins involved in cell cycle block (e.g. cyclin D1, cyclin D3 and pRB) or proteins associated with apoptosis (e.g. surviving, Bcl-$X_L$ and Bcl-2). Both the inventive compositions and baicalein also inhibit 12-LOX activity. However, not all the changes in phosphorylation status of these important proteins is identical after treatment with either the inventive compositions or baicalein, suggesting that the mechanism of action of the inventive compositions is complex and is not due to its content of baicalein alone.

TABLE 5

| Activity or content measured in PC3 cells | Treatment with the inventive compositions | Baicalein treatment |
| --- | --- | --- |
| Cytotoxicity | Yes | Yes |
| Cell cycle block | G2/M | Yes |
| 12-LOX activity | ↓ | ↓ |
| pRb content | ↓ | ↓ |
| Rb content | ↑ | ↑ |
| Cyclin D1 | ↓ | ↓ |
| Cyclin D3 | ↓ | ↓ |
| p21 | No change | Strong ↓ |
| P27 | No change | Strong ↓ |
| Bcl-$X_L$ | ↓ | ↓ |
| Bax | No change | ↑ |
| Bcl-2 | ↓ | ↓ |
| pAKT | No change | ↓ |
| survivin | ↓ | ↓ |

↓ indicates reduction, inhibition, or downregulation
↑ indicates enhancement, activation, or upregulation Example 15

Decline in Phosphorylation of Rb Protein Mediated by the Inventive Compositions

Figure 19A:
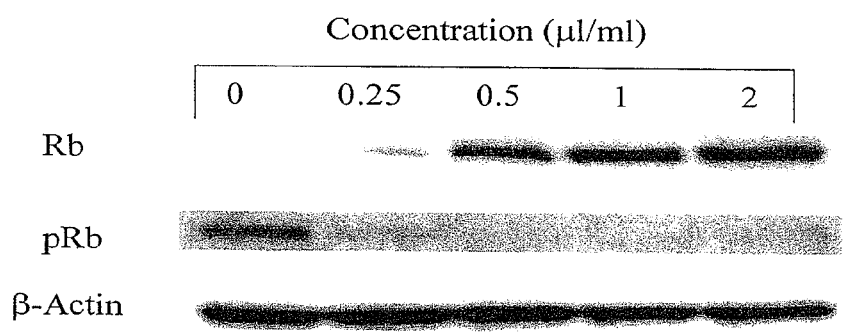
FIG. 19(A) is a photograph of a Western blot depicting retinoblastoma protein as both unphosphorylated (Rb) and phosphorylated (pRb) proteins.
Figure 19B:
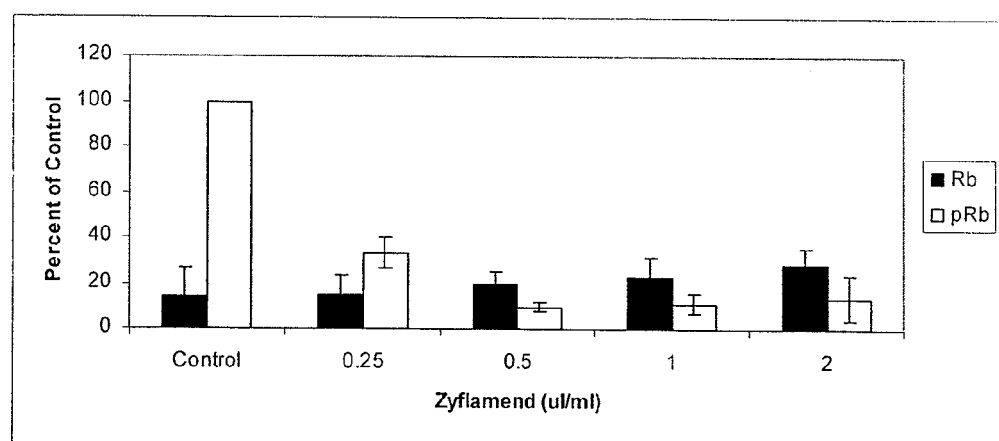
FIG. 19(B) is a graph depicting the data in FIG. 19(A) after scanning the gels in a photometric scanning device to permit quantification of the density of the bands.

As shown in FIG. 19(A), there is a concentration dependent inhibition of Rb phosphorylation. Concentrations as low as 0.25 ul/ml significantly reduced pRb compared to controls while the amount of Rb increased as the pRb decreased. The decrease in phosphorylation of Rb protein occurred at concentrations of the inventive compositions also associated with $G_2/M$ cell cycle block and early apoptosis. Quantitation of the Western blot data is presented in FIG. 19(B).

Shown in FIG. 19(A) is a Western blot of retinoblastoma protein as both unphosphorylated (Rb) and phosphorylated (pRb) proteins. The bottom band (β-actin) is shown only as a loading control. The data are derived from PC3 cells treated with the inventive compositions at the concentrations shown for a 24 hr period of time. Cells were then lysed and proteins separated on a gel. The presence of Rb or pRb proteins was determined with use of specific monoclonal antibodies. The data are also shown in the bottom figure after scanning the gels in a photometric scanning device to permit quantification of the density of the bands. The data show that even at a concentration of 0.25 ul/ml of the inventive compositions there is a clear suppression of pRb (phosphorylated form) and an increase in Rb (nonphosphorylated form).

The decrease in Rb phosphorylation occurred at multiple amino acid sites including T356 (59% decrease relative to control), S807 (62% ↓), T821 (62% ↓) and T826 (78% ↓; other data not shown) resulting from incubation of PC3 cells with the inventive compositions at a concentration of 2 ul/ml for 24 hr.

TABLE 6

Protein phosphorylation screening data from PC3 cells treated with the inventive compositions[a]

| Protein | Phosphorylation site | Change (%) in treated sample relative to controls |
|---|---|---|
| Rb | S807 | −62 |
| Rb | T356 | −59 |
| Rb | T821 | −62 |
| Rb | T826 | −78 |
| STAT1 | S727 | −38 |
| Fos | T232 | +383 |
| HspB1 | S82 | +421 |
| p21 | S144/S141/S154 | +136 |

[a]Abbreviations are as follows: PC3, androgen insensitive human prostate cancer; Rb, retinoblastoma protein; STAT1, signal transducer and activator of transcription 1; Fos, Fos-c FBJ murine osteosarcoma oncoprotein-related transcription factor; HspB1, heat shock 27 kDa protein; p21, p21-activated protein serine kinase.

Example 16

Figure 20A:
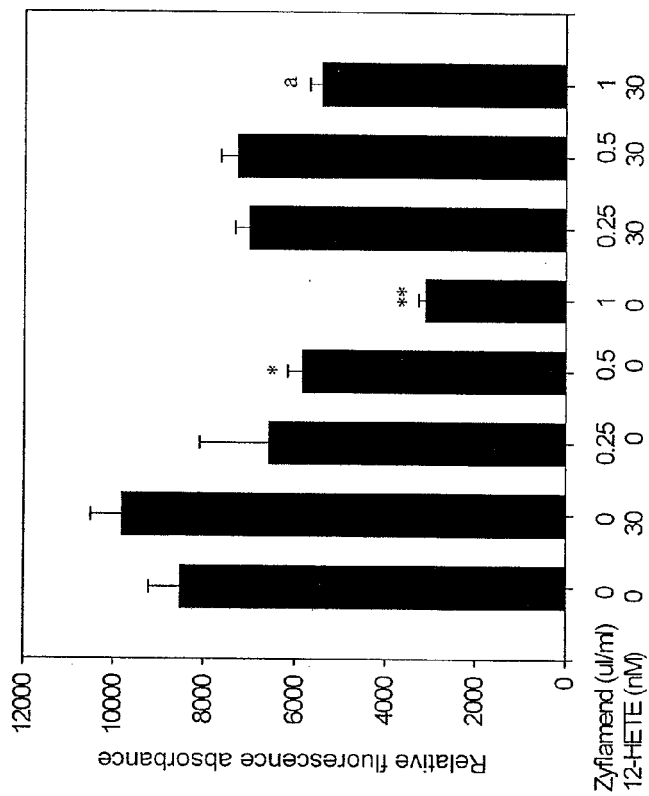
FIG. 20(A) is a graph depicting PC3 cells treated with the inventive compositions at the indicated concentrations and the inhibition of cell proliferation.
Figure 20B:
FIG. 20(B), is a photograph of a Western blot depicting a concentration dependent decline in expression of pRb produced by the inventive compositions.

Ability of 12-HETE to Block Inhibition of PC3 Proliferation by the Inventive Compositions As shown in FIG. 20(A) and FIG. 20(B), addition of $PGE_2$ or 5-HETE to PC3 cells treated with growth inhibitory concentrations of the inventive compositions failed to block cellular proliferation. In contrast, FIG. 20(A) shows that 12-HETE added to cells treated with the inventive compositions (1 ul/ml; a concentration that produced potent induction of apoptosis and $G_2/M$ arrest) resulted in a near doubling of cell proliferation although not back to control untreated cell levels.

Addition of 12-HETE (designated as 12-H) also resulted in a block of the ability of the inventive compositions to reverse the phosphorylated status of RB protein in PC3 cells (FIG. 20(B)); neither PGE2 nor 5-HETE (designated as 5H) had any effect on the ability of the inventive compositions to alter pRb status. Finally, 12-HETE added to PC3 cells also provided partial reversal of the inventive compositions mediated G2/M block thus pointing out the importance of this particular eicosanoid in inhibition of PC3 cell proliferation mediated by the inventive compositions.

Thus, as shown in FIG. 20(A) in an "add-back" experiment, PC3 cells were treated with the inventive compositions at the indicated concentrations which resulted in a concentration dependent inhibition of cell proliferation (relative fluorescence indicates numbers of cells). Addition of 12-HETE, the product of 12-lipoxygenase, resulted in a modest increase in PC3 cell growth. However, addition of 12-HETE to cells treated with the inventive compositions largely blocked tumor cell proliferation inhibition mediated by the inventive compositions.

As shown in FIG. 20(B), the inventive compositions produced a concentration dependent decline in expression of pRb. Adding either 5-HETE (5-H) or PGE2 did not block this effect. Addition of the 12-LOX product, 12-HETE, however, partially returned the production of pRb expression. Taken together these data show that the inhibition of 12-LOX mediated by the inventive compositions is important in that 12-HETE can block anti-proliferative activity and the ability of the inventive compositions to restore expression of the tumor suppressor protein Rb.

REFERENCES

The following literature references are believed to useful to an understanding of the inventive subject matter in the context of its place in the relevant art. Citation here is not to be construed as an assertion or admission that any reference cited is material to patentability of the inventive subject matter. Applicants will properly disclose information material to patentability in an Information Disclosure Statement. The content of each reference is hereby incorporated in their entirety.

1. Singh, S. and Aggarwal, B. B. (1995) Activation of transcription factor NF-kappa B is suppressed by curcumin (diferuloylmethane) [corrected]. *J. Biol. Chem.*, 270, 24995-25000.

2. Aggarwal, S., Ichikawa, H., Takada, Y., Sandur, S. K., Shishodia, S. and Aggarwal, B. B. (2006) Curcumin (diferuloylmethane) down-regulates expression of cell proliferation and antiapoptotic and metastatic gene products through suppression of I kappa B alpha kinase and Akt activation. *Mol. Pharmacol.*, 69, 195-206.

3. Plummer, S. M., Holloway, K. A., Manson, M. M., Munks, R. J., Kaptein, A., Farrow, S. and Howells, L. (1999) Inhibition of cyclooxygenase 2 expression in colon cells by the chemopreventive agent curcumin involves inhibition of NF kappa B activation via the NIK/IKK signalling complex. *Oncogene*, 18, 6013-6020.

4. Paschka, A. G., Butler, R. and Young, C. Y. (1998) Induction of apoptosis in prostate cancer cell lines by the green tea component, (−)-epigallocatechin-3-gallate. *Cancer Lett*, 130, 1-7.

5. Kim, D. S., Kim, H. R., Woo, E. R., Hong, S. T., Chae, H. J. and Chae, S. W. (2005) Inhibitory effects of rosmarinic acid on adriamycin-induced apoptosis in H9c2 cardiac muscle cells by inhibiting reactive oxygen species and the activations of c-Jun N-terminal kinase and extracellular signal-regulated kinase. *Biochem. Pharmacol.*, 70, 1066-1078.

6. Huang, S. S. and Zheng, R. L. (2005) Rosmarinic acid inhibits angiogenesis and its mechanism of action in vitro. *Cancer Lett*.

7. Shishodia, S., Majumdar, S., Banerjee, S. and Aggarwal, B. B. (2003) Ursolic acid inhibits nuclear factor-kappaB activation induced by carcinogenic agents through suppression of I kappa B alpha kinase and p65 phosphorylation: correlation with down-regulation of cyclooxygenase 2, matrix metalloproteinase 9, and cyclin D1. *Cancer Res.*, 63, 4375-4383.

8. Choi, Y. H., Baek, J. H., Yoo, M. A., Chung, H. Y., Kim, N. D. and Kim, K. W. (2000) Induction of apoptosis by ursolic acid through activation of caspases and downregulation of c-IAPs in human prostate epithelial cells. *Int. J. Oncol.*, 17, 565-571.

9. Kim, S. O., Kundu, J. K., Shin, Y. K., Park, J. H., Cho, M. H., Kim, T. Y. and Surh, Y. J. (2005) [6]-Gingerol inhibits COX-2 expression by blocking the activation of p38 MAP kinase and NF-kappaB in phorbol ester-stimulated mouse skin. *Oncogene*, 24, 2558-2567.

10. Atsumi, T., Murakami, Y., Shibuya, K., Tonosaki, K. and Fujisawa, S. (2005) Induction of cytotoxicity and apoptosis and inhibition of cyclooxygenase-2 gene expression, by curcumin and its analog, alpha-diisoeugenol. *Anticancer Res.*, 25, 4029-4036.

11. Tjendraputra, E., Tran, V. H., Liu-Brennan, D., Roufogalis, B. D. and Duke, C. C. (2001) Effect of ginger constituents and synthetic analogues on cyclooxygenase-2 enzyme in intact cells. *Bioorg. Chem.*, 29, 156-163.

12. Manna, S. K., Mukhopadhyay, A. and Aggarwal, B. B. (2000) Resveratrol suppresses TNF-induced activation of nuclear transcription factors NF-kappa B, activator protein-1, and apoptosis: potential role of reactive oxygen intermediates and lipid peroxidation. *J. Immunol.*, 164, 6509-6519.

13. Fukuda, K., Hibiya, Y., Mutoh, M., Koshiji, M., Akao, S. and Fujiwara, H. (1999) Inhibition by berberine of cyclooxygenase-2 transcriptional activity in human colon cancer cells. *J. Ethnopharmacol.*, 66, 227-233.

14. Kelm, M. A., Nair, M. G., Strasburg, G. M. and DeWitt, D. L. (2000) Antioxidant and cyclooxygenase inhibitory phenolic compounds from Ocimum sanctum Linn. *Phytomedicine*, 7, 7-13.

15. Bemis, D. L., Capodice, J. L., Anastasiadis, A. G., Katz, A. E. and Buttyan, R. (2005) Zyflamend, a unique herbal preparation with nonselective COX inhibitory activity, induces apoptosis of prostate cancer cells that lack COX-2 expression. *Nutr. Cancer*, 52, 202-212.

16. Aggarwal, B. B. (2004) Nuclear factor-kappaB: the enemy within. *Cancer Cell*, 6, 203-208.

17. Anto, R. J., Mukhopadhyay, A., Shishodia, S., Gairola, C. G. and Aggarwal, B. B. (2002) Cigarette smoke condensate activates nuclear transcription factor-kappaB through phosphorylation and degradation of IkappaB(alpha): correlation with induction of cyclooxygenase-2. *Carcinogenesis*, 23, 1511-1518.

18. Bharti, A. C., Takada, Y., Shishodia, S. and Aggarwal, B. B. (2004) Evidence that receptor activator of nuclear factor (NF)-kappaB ligand can suppress cell proliferation and induce apoptosis through activation of a NF-kappaB independent and TRAF6-dependent mechanism. *J. Biol. Chem.*, 279, 6065-6076.

19. Takada, Y., Ichikawa, H., Badmaev, V. and Aggarwal, B. B. (2006) Acetyl-11-ketobeta-boswellic acid potentiates apoptosis, inhibits invasion, and abolishes osteoclastogenesis by suppressing NF-kappaB and NF-kappaB-regulated gene expression. *J. Immunol.*, 176, 3127-3140.

20. Chaturvedi, M. M., Mukhopadhyay, A. and Aggarwal, B. B. (2000) Assay for redox-sensitive transcription factor. *Methods Enzymol.*, 319, 585-602.

21. Abu-Amer, Y. and Tondravi, M. M. (1997) NF-kappaB and bone: the breaking point. *Nat. Med.*, 3, 1189-1190.

22. Liotta, L. A., Thorgeirsson, U. P. and Garbisa, S. (1982) Role of collagenases in tumor cell invasion. *Cancer Metastasis Rev.*, 1, 277-288.

23. Van Antwerp, D. J., Martin, S. J., Kafri, T., Green, D. R. and Verma, I. M. (1996) Suppression of TNF-alpha-induced apoptosis by NF-kappaB. *Science*, 274, 787-789.

24. Wang, C. Y., Mayo, M. W. and Baldwin, A. S., Jr. (1996) TNF- and cancer therapy induced apoptosis: potentiation by inhibition of NF-kappaB. *Science*, 274, 784-787.

25. Yamamoto, K., Arakawa, T., Ueda, N. and Yamamoto, S. (1995) Transcriptional roles of nuclear factor kappa B and nuclear factor-interleukin-6 in the tumor necrosis factor alpha-dependent induction of cyclooxygenase-2 in MC3T3-E1 cells. *J. Biol. Chem.*, 270, 31315-31320.

26. Esteve, P. O., Chicoine, E., Robledo, O., Aoudjit, F., Descoteaux, A., Potworowski, E. F. and St-Pierre, Y. (2002) Protein kinase C-zeta regulates transcription of the matrix metalloproteinase-9 gene induced by IL-1 and TNF-alpha in glioma cells via NF-kappa B. *J. Biol. Chem.*, 277, 35150-35155.

27. van de Stolpe, A., Caldenhoven, E., Stade, B. G., Koenderman, L., Raaijmakers, J. A., Johnson, J. P. and van der Saag, P. T. (1994) 12-O-tetradecanoylphorbol-13-acetate and tumor necrosis factor alpha-mediated induction of intercellular adhesion molecule-1 is inhibited by dexamethasone. Functional analysis of the human intercellular adhesion molecular-1 promoter. *J. Biol. Chem.*, 269, 6185-6192.

28. Zhu, L., Fukuda, S., Cordis, G., Das, D. K. and Maulik, N. (2001) Anti-apoptotic protein survivin plays a significant role in tubular morphogenesis of human coronary arteriolar endothelial cells by hypoxic preconditioning. *FEBS Lett.*, 508, 369-374.

29. Chu, Z. L., McKinsey, T. A., Liu, L., Gentry, J. J., Malim, M. H. and Ballard, D. W. (1997) Suppression of tumor necrosis factor-induced cell death by inhibitor of apoptosis c-IAP2 is under NF-kappaB control. *Proc. Natl. Acad. Sci. USA.*, 94, 10057-10062.

30. You, M., Ku, P. T., Hrdlickova, R. and Bose, H. R., Jr. (1997) ch-IAP1, a member of the inhibitor-of-apoptosis protein family, is a mediator of the antiapoptotic activity of the v-Rel oncoprotein. *Mol. Cell. Biol.*, 17, 7328-7341.

31. Catz, S. D. and Johnson, J. L. (2001) Transcriptional regulation of bcl-2 by nuclear factor kappa B and its significance in prostate cancer. *Oncogene*, 20, 7342-7351.

32. Stehlik, C., de Martin, R., Kumabashiri, I., Schmid, J. A., Binder, B. R. and Lipp, J. (1998) Nuclear factor (NF)-kappaB-regulated X-chromosome-linked iap gene expression protects endothelial cells from tumor necrosis factor alpha-induced apoptosis. *J. Exp. Med.*, 188, 211-216.

33. Tamatani, M., Che, Y. H., Matsuzaki, H., Ogawa, S., Okado, H., Miyake, S., Mizuno, T. and Tohyama, M. (1999) Tumor necrosis factor induces Bcl-2 and Bclx expression through NFkappaB activation in primary hippocampal neurons. *J. Biol. Chem.*, 274, 8531-8538.

34. Schwenzer, R., Siemienski, K., Liptay, S., Schubert, G., Peters, N., Scheurich, P., Schmid, R. M. and Wajant, H. (1999) The human tumor necrosis factor (TNF) receptor-associated factor 1 gene (TRAF1) is up-regulated by cytokines of the TNF ligand family and modulates TNF-induced activation of NF-kappaB and c-Jun N-terminal kinase. *J. Biol. Chem.*, 274, 19368-19374.

35. Kreuz, S., Siegmund, D., Scheurich, P. and Wajant, H. (2001) NF-kappaB inducers upregulate cFLIP, a cycloheximide-sensitive inhibitor of death receptor signaling. *Mol. Cell. Biol.*, 21, 3964-3973.

36. Shishodia, S. and Aggarwal, B. B. (2004) Nuclear factor-kappaB activation mediates cellular transformation, proliferation, invasion angiogenesis and metastasis of cancer. *Cancer Treat Res.*, 119, 139-173.

37. Takada, Y., Singh, S. and Aggarwal, B. B. (2004) Identification of a p65 peptide that selectively inhibits NF-kappa B activation induced by various inflammatory stimuli and its role in down-regulation of NF-kappaB-mediated gene expression and up-regulation of apoptosis. *J. Biol. Chem.*, 279, 15096-15104.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. A method for modulating an eicosanoid metabolic process in cells of an animal in need thereof, comprising
    administering to the animal an amount of a composition effective for regulating the activity of an eicosanoid oxygenase;
    wherein the composition comprises therapeutically effective amounts of supercritical extracts of rosemary, turmeric, oregano and ginger; and therapeutically effective amounts of hydroalcoholic extracts of holy basil, ginger, turmeric, Scutellaria baicalensis, rosemary, green tea, huzhang, Chinese goldthread, and barberry; and
    wherein (A) the weight ratio of the supercritical extract of ginger to the hydroalcoholic extract of ginger ranges from about 0.8:1 to about 1.4:1, (B) the weight ratio of the hydroalcoholic extract of turmeric to the supercritical extract of turmeric ranges from about 8:1 to about 12:1, (C) the weight ratio of the supercritical extract of rosemary to the hydroalcoholic extract of rosemary ranges from about 1.6:1 to about 2.4:1, or (D) a combination thereof.

2. The method of claim 1, wherein the supercritical extract of rosemary is at a concentration ranging from about 10.0% to about 16.0% by weight of the total composition.

3. The method of claim 1, wherein the supercritical extract of turmeric is at a concentration ranging from about 1.0% to about 1.5% by weight of the total composition.

4. The method of claim 1, wherein the supercritical extract of oregano is at a concentration ranging from about 4.0% to about 6.0% by weight of the total composition.

5. The method of claim 1, wherein the supercritical extract of ginger is at a concentration ranging from about 5.5% to about 8.5% by weight of the total composition.

6. The method of claim 1, wherein the hydroalcoholic extract of ginger is at a concentration ranging from about 4.5% to about 7.5% by weight of the total composition.

7. The method of claim 1, wherein the hydroalcoholic extract of turmeric is at a concentration ranging from about 10.0% to about 16.0% by weight of the total composition.

8. The method of claim 1, wherein the hydroalcoholic extract of rosemary is at a concentration ranging from about 5.5% to about 8.0% by weight of the total composition.

9. The method of claim 1, wherein the hydroalcoholic extract of holy basil is at a concentration ranging from about 10.0% to about 16.0% by weight of the total composition.

10. The method of claim 1, wherein the hydroalcoholic extract of green tea is at a concentration ranging from about 10.0% to about 16.0% by weight of the total composition.

11. The method of claim 1, wherein the hydroalcoholic extract of huzhang is at a concentration ranging from about 8.0% to about 12.0% by weight of the total composition.

12. The method of claim 1, wherein the hydroalcoholic extract of Chinese goldthread is at a concentration ranging from about 4.0% to about 6.0% by weight of the total composition.

13. The method of claim 1, wherein the hydroalcoholic extract of barberry is at a concentration ranging from about 4.0% to about 6.0% by weight of the total composition.

14. The method of claim 1, wherein the hydroalcoholic extract of Scutellaria baicalensis is at a concentration ranging from about 2.0% to about 3.0% by weight of the total composition.

15. The method of claim 1, wherein the cells are cancer cells.

16. The method of claim 15 wherein the cancer cells comprise prostate cancer cells, breast cancer cells, lung cancer cells, colon cancer cells, or a combination thereof.

17. The method of claim 16, wherein the eicosanoid metabolic process is aberrant metabolism associated with cellular transformation to cancer, cancer cell proliferation, cancer cell metastasis, cancer cell invasiveness, cancer cell-modulated angiogenesis, cancer cell-modulated apoptosis suppression, or a combination thereof.

18. The method of claim 1, wherein the animal is human.

* * * * *